(12) United States Patent
Parker et al.

(10) Patent No.: US 8,055,324 B1
(45) Date of Patent: Nov. 8, 2011

(54) RAPID REPORTS

(75) Inventors: Don M. Parker, Los Angeles, CA (US);
Ken Pfeiffer, Santa Barbara, CA (US)

(73) Assignee: Sonultra Corporation, Los Angeles, CA (US)

( * ) Notice: Subject to any disclaimer, the term of this patent is extended or adjusted under 35 U.S.C. 154(b) by 1465 days.

(21) Appl. No.: 11/138,874

(22) Filed: May 25, 2005

Related U.S. Application Data

(60) Provisional application No. 60/574,610, filed on May 25, 2004.

(51) Int. Cl.
| | |
|---|---|
| *A61B 5/05* | (2006.01) |
| *A61B 8/00* | (2006.01) |
| *G06Q 50/00* | (2006.01) |
| *G06F 3/00* | (2006.01) |

(52) U.S. Cl. .............. 600/407; 600/437; 705/3; 715/744
(58) Field of Classification Search .................. 600/440, 600/407, 437; 705/2, 3; 382/128, 305; 128/920, 128/922, 906; 700/214; 715/700, 965, 968, 715/744

See application file for complete search history.

(56) References Cited

U.S. PATENT DOCUMENTS

| | | | |
|---|---|---|---|
| 6,091,981 A * | 7/2000 | Cundari et al. ............... | 600/407 |
| 6,260,021 B1 | 7/2001 | Wong et al. | |
| 6,581,020 B1 | 6/2003 | Buote et al. | |
| 6,674,879 B1 * | 1/2004 | Weisman et al. ............. | 382/128 |
| 6,684,276 B2 * | 1/2004 | Walker et al. .................. | 710/73 |
| 6,689,055 B1 | 2/2004 | Mullen et al. | |
| 6,785,410 B2 * | 8/2004 | Vining et al. ................. | 382/128 |
| 7,252,638 B2 * | 8/2007 | Kahn et al. .................... | 600/443 |
| 2002/0095313 A1 * | 7/2002 | Haq ................................. | 705/2 |
| 2003/0018245 A1 * | 1/2003 | Kaufman et al. ............. | 600/407 |
| 2003/0073895 A1 * | 4/2003 | Nields et al. .................. | 600/407 |

OTHER PUBLICATIONS

Nissan et al., "Computer-based inpatient medical record in colorectal surgery", Diseases of the Colon and Rectum, Feb. 2000, vol. 43, No. 2, pp. 242-248.*
"PointDx: Our Products-Workstation", [online] http://www.pointdx.com/ourProducts_workstation [retrieved] May 16, 2005.

\* cited by examiner

*Primary Examiner* — Long V. Le
*Assistant Examiner* — Katherine Fernandez
(74) *Attorney, Agent, or Firm* — Fish & Richardson P.C.

(57) ABSTRACT

The present disclosure includes systems and techniques relating to documentation and reporting systems for use with diagnostic medical imaging procedures. In general, in one implementation, an ultrasound imaging system includes: one or more signal processing subsystems; one or more ultrasound transducer probes coupled with the one or more signal processing subsystems; and a computer-readable medium including encoded thereon program instructions operable to cause the ultrasound imaging system to present a user interface that enables documentation by exception of an ultrasound exam, wherein the user interface provides access to prior exam findings and is configured at least in part based on the prior exam findings, and the program instructions generate an electronic report including the documentation of the ultrasound exam, and including, when indicated as clinically relevant, the prior exam findings.

19 Claims, 19 Drawing Sheets

Sonultra Corporation
Outpatient Obstetrical Ultrasound Report

Page 1 of 1

Patient Name: Example, Sample　　Referring Provider: Dr. Walter Disney　　Study Date: 02/15/05
Patient ID#: SAMEXAM　　Age: 46　D.O.B.:　　LMP: 12/15/04　G:1
Probes:　　Transvag+Transab　　Referred For: Advanced MA　　Habitual Aborter

DESCRIPTIVE DATA

Yolk SAC: Present　　4.0 cm

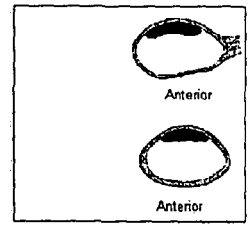

Anterior

Anterior

Placenta- 　　Appearance: No Anomalies Obs
　　Cord Insertion: No Anomalies Obs　Gest. Location: Intrauterine
Fetal Heart- Rhythm: Regular　　BPM= 136
Amniotic Fluid- Volume WNL　　AFI: 22.0

FETAL ANATOMY SURVEY　Viable

No Anomalies Observed- HEART: Location/Size

| BEST GA ANALYSIS - | 6 wks 0 days | ± .5 wk | Based on: LMP (user selected) | | |
|---|---|---|---|---|---|
| Current Study # 1 | YS | SAC | CRL | Exam　GA (wk)　EDD | |
| MEAS (CM) | 4.0 | 1.2 | .6 | Current : 6.4 | 10/08/05 |
| PRED GA(wk) | | 6.1 | 6.4 | LMP:　　8.9 | 09/21/05 |

ADDITIONAL BIOMETRY
Nuchal Translucency= 1.33 mm

MATERNAL ANATOMY SURVEY

*Anomalies Observed- Cervix:Shortened Cervix(L=3.4 cm)*
No Anomalies Observed- Maternal Kidneys, Uterus, R Ovary, L Ovary, Endometrial Stripe(L=4.0 mm);
　　　　　　　Pessary:Present; Cerclage:Present; Beaking:Absent; Funneling:Mild; Prolapse:Present; Cul
　　　　　　　de Sac:Visualized, Adnexa This report has been electronically signed.
Dr. Parker 10700 Santa Monica Blvd. Suite 16, Los Angeles, CA 90025

| Example, Sample Study # 2 5/22/2005 Gestation 1 Baby A Dr. Walter Disney (20+ wk) |

Placenta
- Longitudinal : Posterior
- Transverse : Posterior
- Appearance : No Anomalies Obs
- Cord Vessels : 3
- Grade : II
- Chorionicity :

Fetal Position
- Presentation : *Complete Breech
- Head : Maternal Lt
- Spine : Maternal Lt
- Gest Location :
- Yolk SAC :
- Probes Used : Transvag+Transab

Fetal Heart 133 bpm
- 4 Chmbr View : No Anomalies Obs
- Location/Size : No Anomalies Obs
- Rhythm : Regular
- L Outflow Tract : No Anomalies Obs
- R Outflow Tract : No Anomalies Obs
- Venous System : No Anomalies Obs

Fetal Anatomy Viable                 *Anomaly  +Notable
Gender : Male
- Intracranial : No Anomalies Obs
- Facial : No Anomalies Obs
- Thorax : No Anomalies Obs
- Spine : *Meningocele
- Up Extrem : No Anomalies Obs
- Low Extrem : No Anomalies Obs
- Abd Wall : *Edema
- Abd Cavity : No Anomalies Obs
- Stomach Fluid : No Anomalies Obs
- Bladder Fluid : No Anomalies Obs
- Right Kidney : No Anomalies Obs
- Left Kidney : No Anomalies Obs

Maternal Anatomy ☐ Transvagina
- Cervix : No Anomalies Obs
- Cervix Length : 4.3 cm

Amniotic Fluid AFI : 13.7
- Deepest Pool : 0.0   AFI 45 %
- Findings : Volume WNL

Biometry   Gestational Age Estimate : 20.4 wk   Based on: Earliest GA (user selected)

|  | BPD | HC | AD AC | FL | HUM | OFD | CER | CM |
|---|---|---|---|---|---|---|---|---|
| Measurement (cm) : | 5.0 | 17.0 | 12.0 | 3.0 | 0.0 | 0.0 | 0.0 | 0.0 |
| Predicted Age (wk) : | 20.6 | 19.6 | 17.7 | 20.4 | | | | |
| Predicted (+2SD) : | 18-23 | 17-22 | 15-20 | 18-23 | | | | |
| Percentile : | 77 | 11 | 1 | 9 | | | | |

0 lb 9 oz
FW = 249 gm
Range =
Pct =

Demographics  Custom  Comments  Pulsed Doppler   Reporting Physician : Dr. Parker
BPP  CVS  NST  Genetic Sono  Amnio           Sonographer : Sarah Sounder Custom Set [Full Anatomical S ▼]  [Load Custom]  Save Custom  Clear  Images  Close

Sonultra Corporation
Outpatient Obstetrical Ultrasound Report
Page 1 of 2

| | | |
|---|---|---|
| Patient Name: Example, Sample | Referring Provider: Dr. Walter Disney | Study Date: 05/22/05 |
| Patient ID#: SAMEXAM | Age: 46 D.O.B.: | LMP: 12/10/04 G:1 |
| Probes: Transvag+Transab | Referred For: Advanced MA | Family History |

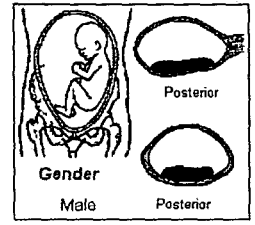

DESCRIPTIVE DATA
Fetal Position- Presentation: _Complete Breech_ Head: Maternal Lt. Spine: Maternal Lt.
Placenta- Grade: II Cord Vessels: 3 Appearance: No Anomalies Obs
    Cord Insertion: No Anomalies Obs
Fetal Heart- Rhythm: Regular     BPM= 133
Amniotic Fluid- Volume WNL     AFI: 13.7 _(45%)_

Gender: Male    Posterior

FETAL ANATOMY SURVEY    Viable

_Anomalies Observed- Abd Wall:Edema; Spine:Meningocele_
No Anomalies Observed- INTRACRANIAL: Lat Ventricles, Third Ventricle, Fourth Ventricle, Choroid Plexus, Thalami,
    Corpus Callosum, Midline, Cerebellum, Cisterna Magna; Parenchyma Location:Frontal
    FACIAL: Orbits, Nostrils, Palate, Lips, Maxilla, Mandible, Nasal Bone, Neck, Ear
    HEART: 4 Chamber View, R Outflow Tracts, L Outflow Tracts, Location/Size, Venous System
    TRUNK: Abd Cavity, Stomach Fluid, Bladder Fluid, R Kidney, L Kidney, Thorax, Spine
    Cervical, Spine Thoracic, Spine Lumbar, Spine Sacrum, Spine Coccyx
    EXTREMITIES: Upper Extremities, Arms, Hands, Fingers, Lower Extremities, Legs, Feet, Toes

Fetal EchoCardiography B Mode
No Anomalies Observed- FOUR CHAMBER VIEW: Atrial Chambers:Atrial equal in size; Foramen Ovale:Foramen ovale
    flow in left atrial chamber; L Pulm Veins:Two pulmonary veins entering left atrium; R Pulm
    Veins:Two pulmonary veins entering left atrium;    LOCATION/SIZE: Heart Location,
    Chest:Atrial equal in size; Heart Size:Ventricular chambers equal in size;    R OUTFLOW
    TRACT: Main Pulm Artery:Septum primum present; R Pulm Artery:Foramen ovale flow in left
    atrial c; L Pulm Artery:Normal size and position;    L OUTFLOW TRACT: Ascending
    Aorta:Atrial equal in size; Aortic Arch:Ventricular chambers equal in size;    VENOUS
    SYSTEM: Inferior Vena Cava:Atrial equal in size; Superior Vena Cava:Ventricular chambers
    equal in size; Ductus Venosis:Septum primum present; L Hepatic Veins:Normal anatomy
Poorly Seen- Interatrial Septum

Fetal EchoCardiography Color
No Anomalies Observed- FOUR CHAMBER VIEW: Atrial Chambers:Blood flow normal systole and diastole; Interatrial
    Septum:No abnormal flow across septum; Foramen Ovale:No abnormal flow across foramen
    ovale;    L OUTFLOW TRACT: Ascending Aorta:Normal flow direction;    VENOUS SYSTEM:
    Superior Vena Cava:Normal flow direction

BIOPHYSICAL PROFILE- 8/8
Movement= 2   Tone= 2   Breathing= 2   AFV= 2

BEST GA ANALYSIS - 20 wks 3 days   ± 1.5 wk    Based on: Earliest GA (user selected)

| Current Study # 2 | BPD (%) | HC (%) | FL (%) | AC (%) | | Exam | GA (wk) | EDD | EFW % |
|---|---|---|---|---|---|---|---|---|---|
| MEAS (CM) | 5.0 77% | 17.0 11% | 3.0 9% | _12.0 1%_ | | Earliest: | 20.4 | 10/06/05 | |
| PRED GA(wk) | 20.6 | 19.6 | 20.4 | 17.7 | | Current: | 19.3 | 10/14/05 | |
| | | | | | | LMP: | 23.3 | 09/16/05 | |

EST. FETAL WEIGHT - 249 gm    (213-286 gm)    0lb 9oz

Sonultra Corporation
Outpatient Obstetrical Ultrasound Report

Page 1 of 2

| | | |
|---|---|---|
| Patient Name: Example, Sample | Referring Provider: Dr. Walter Disney | Study Date: 05/22/05 |
| Patient ID#: SAMEXAM | Age: 46 D.O.B.: | LMP: 12/10/04 G:1 |
| Probes: Transvag+Transab | Referred For: Advanced MA | Family History |

DESCRIPTIVE DATA

Fetal Position- Presentation: *Complete Breech* Head: Maternal Lt. Spine: Maternal Lt.
Placenta- Grade: II Cord Vessels: 3 Appearance: No Anomalies Obs
       Cord Insertion: No Anomalies Obs
Fetal Heart- Rhythm: Regular        BPM= 133
Amniotic Fluid- Volume WNL        AFI: 13.7 *(45%)*

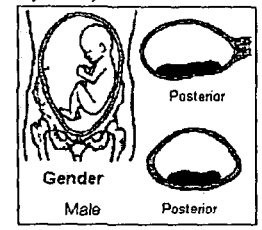

Posterior

Gender
Male    Posterior

FETAL ANATOMY SURVEY    Viable

*Anomalies Observed-* *Abd Wall:Edema; Spine:Meningocele*
No Anomalies Observed- INTRACRANIAL: Lat Ventricles, Third Ventricle, Fourth Ventricle, Choroid Plexus,
    Cerebellum, Cisterna Magna
    FACIAL: Orbits, Lips, Maxilla, Mandible, Nasal Bone
    HEART: 4 Chamber View, R Outflow Tracts, L Outflow Tracts, Location/Size, Venous System
    TRUNK: Abd Cavity, Stomach Fluid, Bladder Fluid, Thorax, Spine Cervical, Spine Thoracic
    EXTREMITIES: Arms, Hands, Fingers, Legs, Feet, Toes

Fetal EchoCardiography B Mode

No Anomalies Observed- FOUR CHAMBER VIEW: Ventricular Chambers:Ventricular chambers equal in size; Foramen
    Ovale:Foramen ovale flow in left atrial chamber; L Pulm Veins:Two pulmonary veins entering
    left atrium; R Pulm Veins:Two pulmonary veins entering left atrium; R OUTFLOW TRACT:
    Main Pulm Artery:Septum primum present; R Pulm Artery:Foramen ovale flow in left atrial c; L
    Pulm Artery:Normal size and position;    L OUTFLOW TRACT: Ascending Aorta:Atrial equal in
    size; Aortic Arch:Ventricular chambers equal in size; Thoracic Aorta:Normal size and
    position;    VENOUS SYSTEM: Inferior Vena Cava:Atrial equal in size; Superior Vena
    Cava:Ventricular chambers equal in size; Ductus Venosis:Septum primum present
Poorly Seen- Interatrial Septum

BIOPHYSICAL PROFILE- 8/8
Movement= 2    Tone= 2    Breathing= 2    AFV= 2

BEST GA ANALYSIS - 20 wks 3 days   ± 1.5 wk    Based on: Earliest GA (user selected)

| Current Study # 2 | BPD (%) | HC (%) | FL (%) | AC (%) | | Exam | GA (wk) | EDD | EFW % |
|---|---|---|---|---|---|---|---|---|---|
| MEAS (CM) | 5.0 77% | 17.0 11% | 3.0 9% | *12.0 1%* | | Earliest: | 20.4 | 10/06/05 | |
| PRED GA(wk) | 20.6 | 19.6 | 20.4 | 17.7 | | Current: | 19.3 | 10/14/05 | |
| | | | | | | LMP: | 23.3 | 09/16/05 | |

EST. FETAL WEIGHT - 249 gm    (213-286 gm)    0lb 9oz

ADDITIONAL BIOMETRY
FL/BPD= 0.60 •••• FL/HC= 0.18 •••• FL/AC= 0.25 •••• HC/AC= 1.42 ••••

MATERNAL ANATOMY SURVEY
No Anomalies Observed- Cervix(L=4.3 cm); Pessary:Present; Cerclage:Present; Beaking:Absent; Funneling:None;
    Prolapse:Present

RAPID REPORTS

CROSS REFERENCE TO RELATED APPLICATIONS

This application claims the benefit of the priority of U.S. Provisional Application Ser. No. 60/574,610, filed May 25, 2004 and entitled "RAPID REPORTS", which application is hereby incorporated by reference.

BACKGROUND

The present application describes systems and techniques relating to documentation and reporting systems for use with diagnostic medical imaging procedures.

Traditional documentation processes for diagnostic imaging procedures have included both computerized and manual reporting solutions and generally involve an inventory type process, where each item considered during the procedure is documented in turn, like checking off items on an inventory list. Traditional computerized reporting solutions have used drop down lists, radio buttons, fill in the blanks, and scroll bars as part of their interface, but still represented a documentation by inventory approach. Such solutions typically offered many questions on many pages that users needed to organize and track in their own heads, thus full documentation of an exam (such as to meet regulatory requirements) was performed after the exam was completed, and the examiner was no longer conducting the exam. Since medical imaging equipment is often expensive and its use in high demand, traditional exam documentation and reporting solutions where often too time consuming to be used during the actual exam (i.e., prior solutions were geared towards doing an exam, reviewing the exam and then documenting the report).

Many off-line computerized solutions try to optimize the user interface by defining each type of exam and dedicating a unique user interface for each exam type. In many cases, the user interface pages contain specified headings requiring the user to go to a specific section to answer a question. Users were often required to keep track of where they have been and what they have done in the user interface by jumping around to each page they have visited. Moreover, many times the only way the user is able to track exactly what has been documented is to first generate, and then look at, the final report.

Many ultrasound scanners also provide an on-board documentation system. These systems typically incorporate a multi-page user interface or a scrollable user interface. When specific exam protocols were addressed in such on-board documentation systems, this was typically handled by developing several user interface pages to handle each and every unique protocol separately.

SUMMARY

The present disclosure includes systems and techniques relating to documentation and reporting systems for use with diagnostic medical imaging procedures.

According to an aspect, a user interface can include a single main window (Primary Page) that shows primary topics, preferably organized so as to appear entirely within the available display area (e.g., with no scroll bars). This main window can be organized to comprehensively address the issues pertaining to an exam in a summary fashion and may be designed to readily enable users to comply with clinical standards required by their community. Additionally, the Primary Page interface can serve as a gateway to address additional details through a comprehensive series of subsidiary windows (e.g., pop-up dialogs) while maintaining a quick snapshot of the progress made in completing an exam. Thus, users can readily expand beyond the protocols defined for a particular exam to address issues outside of those defined by the protocol.

This type of user interface, in combination with documentation by exception, serves to standardize workflow, maximize productivity, and minimize training, while also being flexible enough for the end user to adjust, on the fly and in real time during the course of an exam, to document findings in any order and to any depth, as is appropriate to the given situation. It should be noted that many exams, including diagnostic obstetrics (OB) ultrasound exams are not performed in a linear fashion; the changing position or movement of the fetus often dictates a non-linear approach to an exam.

The Rapid Reports program can be readily customized for a changing clinical environment, allowing monitoring of multiple strict clinical protocols. The user interface can enable efficient documentation of findings, assist users in keeping track of their progress, and reduce documentation time. The program can reside on a freestanding personal computer, or on a medical imaging device, and also be configured to effectively interface with medical equipment. Moreover, because the documentation process is very efficient, exam documentation can readily be performed while the exam is being given, and the program can be loaded and run on the medical imaging equipment (e.g., the ultrasound machine) itself.

The Rapid Reports program can be used to document an exam after the fact but also is efficient enough to document an exam during the exam without interfering with the integrity or performance of the exam. Thus, the Rapid Reports program enables efficient real time documentation that may minimize the potential for errors as information can be documented at the time it is acquired instead of after fact. The Rapid Reports program can document an exam while the exam is being performed, and may only add seconds to the exam, regardless of the complexity of the exam. Moreover, the Rapid Reports program can be customized to comply with regulatory documentation requirements but also be customized to follow the protocols developed by the individual practice.

Subsidiary windows (e.g., pop-up dialogs) can provide additional information on the primary topics found in the single main window of the user interface. These subsidiary windows can provide specific detail for a category of topics. For example, a Facial Survey can either be summarized in the main window or extensive detail about the Facial Survey can be addressed in the subsidiary window on this subject.

The main window of the user interface may automatically adjust to reflect data acquired in an earlier exam. For example, the user interface used for a 6 week old fetus may be very different than the user interface used for a study performed 14 weeks later when the fetus is 20 weeks old. The user interface can automatically adjust to enable the user performing a 20 week exam to focus on what is important.

Within each category of exam, there can be multiple predefined protocols a user may follow. For example, a 20 week exam can be a full anatomical survey, a limited follow-up exam, a targeted exam and/or include various other supplementary procedures. The multiple predefined protocols can be customized by users to address documentation and reporting on expected or anticipated results. This enables a user to document in the same way they work, by exception. When a trained practitioner performs an exam they are reviewing a multitude of issues, however, they do not inventory each item in their head one step at a time. Rather, a trained practitioner goes through the procedure looking for items they should consider while items that fall within the expected or anticipated guidelines are only mentally noted in passing; in other words, the trained practitioner documents findings by exception. The interaction and documentation procedure with the Rapid Reports program is designed to facilitate the usual exam practices of the trained practitioner.

When findings are identified during a previous exam, the user interface for the current exam can also present the findings from the previous exam. Users can then elect to enter changes from the prior findings into the current exam, then carry forward those items existing on the previous exam, as appropriate, into the current exam, thereby not requiring a user to re-enter the prior exam data if there are no changes. This is similar to how a primary single or small practice private practitioner works as they generally add notes to an existing record without reiterating the patient history with each visit.

Many times, a center or physician receiving a referred patient will send a report to the referring physician in order to provide a more comprehensive review of the patient's case; one cannot always rely on the referring physician having access to prior documents for continuity purposes. The ability to carry forward prior information from a prior exam can materially reduce the user's interaction with the computer and can help direct the physician when tracking or following up on a prior exam.

Furthermore, clinical protocols can be incorporated into the reporting process, which can serve to standardize and protect the interest of both patient and physician. A secondary database can be used to manage the relevancy of customizable responses to questions for user defined imaging procedure guidelines (i.e., clinical protocols for performing exams). Enabling a user to customize responses allows a user to follow customized user protocols, which improves efficiency, while also operating under the same user interface page. Thus, the user can change the underlying protocol and functionality of the user interface page and still maintain the same user interface look and feel.

Maintaining the same user interface page regardless of the report can reduces training time and errors, and can also shorten reporting time. For example, the Rapid Reports program can let users standardize and use the same interface page for an 11-14 week fetal exam, 14-20 week fetal exam and a 20-week to term fetal exam.

The user interface can allow for a range of procedures to be performed, even from a user interface page configured for a particular procedure (e.g., a 14-20 week user interface page can still allow the user to accommodate exams that are actually between 12-22 weeks). Building in tolerances for the range of exams a user interface can address helps maintain the flexibility of the solution to accommodate discoveries that may alter the type of exam performed. Thus, the user is provided the ability to adjust for any surprises without interrupting the documentation process, and the program enables development of clinical practice management protocols within a single main window interface for multiple types of ultrasound exams.

Users may define the protocols they want to follow for a particular exam by defining which questions should be addressed as well as their standard default responses. Questions that are generally responded to and have variable responses may have customized responses indicating the user is required to specifically select a response for each such question. Almost every single exam performed has a very limited number of unique observations. By defining the anatomical survey protocols for a particular type of exam, users can standardize their approach and complete an entire exam with only a very limited number of responses. Moreover, having a user interface with a single main window (which may be configured to fit entirely within the display size available) that gives the user an instantaneous overview of what has been done, what needs to be done and when the exam is over, can significantly improve the efficiency of the exam documentation process.

In addition to the various advantages mentioned above, one or more of the following advantages may be provided. Upgrades may be simplified, as users can receive standardized field groups and build into their custom global responses how they want to utilize additional functionality. Training may be simplified because only a few different user interface pages have to be learned within the context of a predefined set of protocols. Time spent interacting with the user interface may be reduced, thereby enabling additional delivery systems for the application (e.g., pen tabs, medical equipment, personal digital assistants (PDAs)). Medical imaging procedure protocols can be standardized for a given practice, while also providing enough flexibility to change the protocols, if the circumstance requires it, on the fly. Therefore, if an exam changes during the course of the exam, the Rapid Reports program can accommodate these changes.

Details of one or more implementations are set forth in the accompanying drawings and the description below. Other features and advantages may be apparent from the description and drawings, and from the claims.

BRIEF DESCRIPTION OF THE DRAWINGS

FIG. 3 shows an early first trimester user interface window after selection of items considered an exception or difficult to anticipate as part of a protocol.

FIG. 4 shows the early first trimester user interface window of FIG. 3 after user-defined custom responses have been loaded.

FIG. 5 shows a report generated for the early first trimester exam.

FIG. 6 shows a 20+ weeks ultrasound exam user interface window after selection of items considered an exception or difficult to anticipate as part of an anatomical survey.

FIG. 8 shows the 20+ weeks ultrasound exam user interface window of FIG. 6 after user-defined custom responses have been loaded for a full anatomical survey protocol.

FIGS. 9A-9J show various pop-up dialog windows triggered by selection of elements in FIG. 8.

FIGS. 10 and 11 show a report generated for the 20+ weeks full anatomical survey protocol.

FIG. 12 shows the 20+ weeks ultrasound exam user interface window of FIG. 6 after user-defined custom responses have been loaded for a limited anatomical survey protocol.

FIGS. 13 and 14 show a report generated for the 20+ weeks limited anatomical survey protocol.

FIG. 15 shows an antepartum ultrasound exam user interface window generated approximately nineteen weeks later.

DETAILED DESCRIPTION

Figure 1:
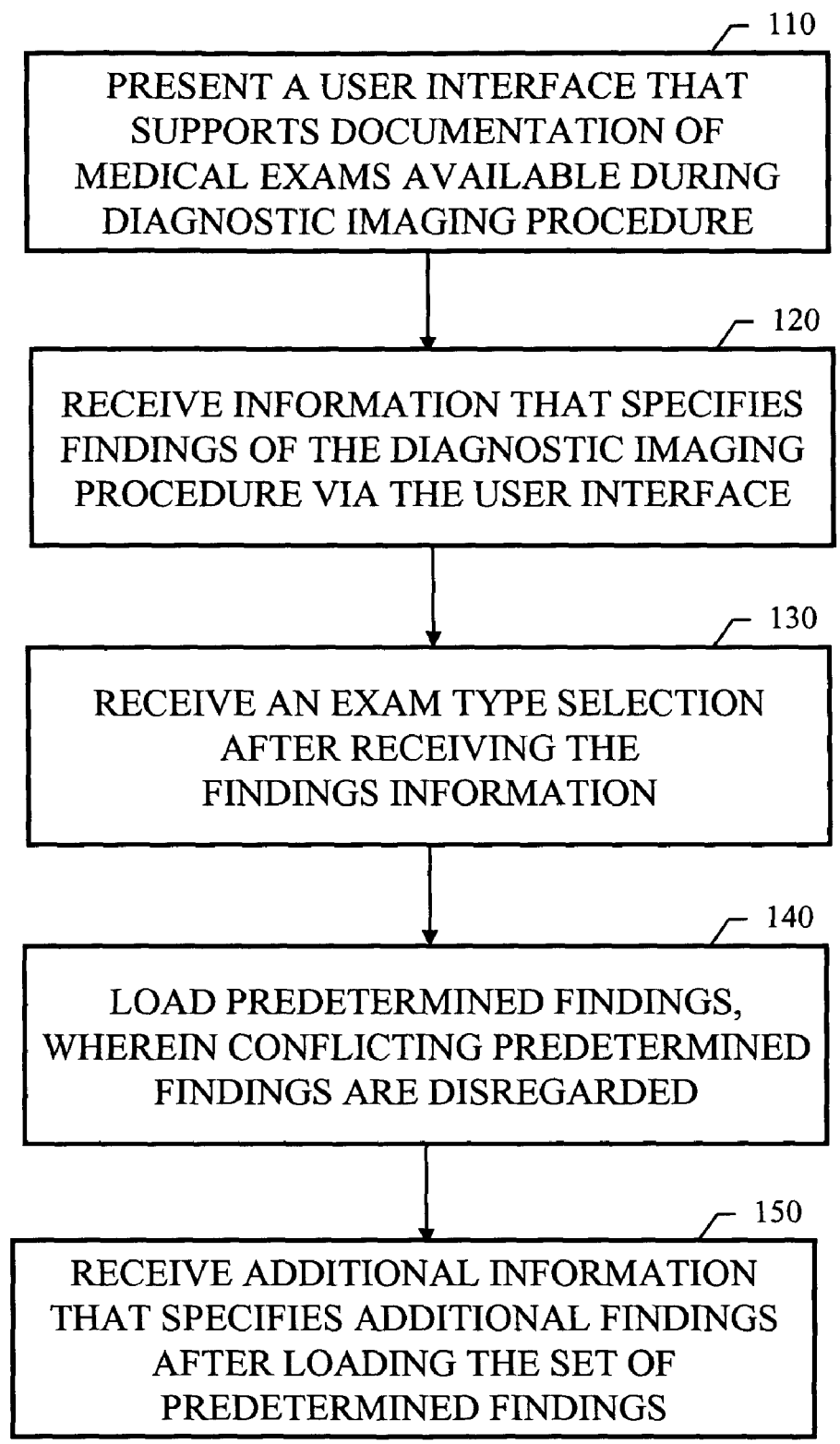
FIG. 1 shows operations of a process of documenting a diagnostic medical imaging procedure.

FIG. 1 shows operations of a process of documenting a diagnostic medical imaging procedure. A user interface that supports documentation of a plurality of medical exams available during a diagnostic medical imaging procedure is presented at 110. The user interface can include a single main window and one or more subsidiary windows, as described further below, that are generated by a program that supports reporting of the plurality of available medical exams.

The program can use a primary database in constructing the user interface, where the primary database manages the various issues a user may address during a diagnostic medical imaging procedure. Moreover, the user interface can integrate the various aspects that can be reported on, and summarize findings made during an exam/study in the single main window, in order to provide an instant assessment of the issues addressed during an exam/study.

Information that specifies findings of the diagnostic medical imaging procedure are received via the user interface at 120. These exam findings can be received using traditional user interface elements, such as drop down lists, radio buttons, and fill-in-the-blank text fields, as well as data generated by and received directly from the ultrasound machine. An exam type selection is received at 130, after receiving the findings information. (Note that the exam type selection can also be made before any findings are received.) The exam type selection corresponds to the diagnostic medical imaging procedure conducted and indicates a selected exam type from a plurality of predefined exam types (e.g., full anatomical survey and limited anatomical survey). Examples of these receiving operations are illustrated further below in connection with FIGS. 3-16.

A set of predetermined findings corresponding to the selected exam type is loaded for the diagnostic medical imaging procedure at 140. These predetermined findings corresponding to the selected exam type can be fully customized by the end-user, including both the fields to be filled and the entries placed in those fields. During the loading of the predetermined findings, any of the predetermined findings in the set that conflict with the received findings information are disregarded. Thus, a user can perform an exam, noting the findings of interest in any order, and then automatically load pertinent negatives for the exam by selecting the predefined type of the exam just conducted after noting the findings of interest. In this way, the documentation and reporting process facilitates the way in which people actually conduct exams, not requiring a user to separately note the negative/standard findings, and not requiring a user to commit to a particular type of exam before the documentation process begins. This is referred to herein as documentation by exception.

The predetermined findings can be maintained by the program in a secondary database that manages the relevant issues of an exam. The predetermined findings can be stored as any number of user-defined clinical protocols, where a clinical protocol defines a type of exam that can be given and a set of global custom responses to the questions addressed by the examiner, during the imaging procedure, for that type of exam. Thus, the end user can define their protocols for diagnostic medical imaging according to their own practice, and these protocols can be as strict as desired. By managing the relevance of issues examined based upon the protocols established by the end user, the user only needs to address issues that fall outside the expected result. This serves to minimize interaction with the user interface and thereby make the documentation process more efficient.

The exam type selection can be made at the very end of the exam, or in the middle of the exam. Thus, additional information that specifies additional findings of the diagnostic medical imaging procedure can be received via the user interface at 150, after loading the set of predetermined findings. This additional information can specify additional findings that change prior findings, both from the received information (i.e., noted exceptions to the expected findings) and from non-conflicting findings of the set of predetermined findings (i.e., automatically loaded pertinent negatives/expected findings).

In addition, the user is always' free to address additional questions during an exam, either before or after loading the custom responses of a defined protocol, even when those additional questions are not part of the defined protocol. A user can select a predefined exam type while still being able to expand the comprehensiveness of an exam without additional customization of exam types (i.e., without having to create a new clinical protocol for every possible exam situation). This is important because often the exact type of exam needed can be difficult to determine up front. For example, in obstetrics ultrasounds exams, it is sometimes difficult to precisely define the gestational age (GA) of a fetus, and the issues of a late first trimester exam are different than the issues of an early second trimester exam. Users are thus provided the ability to easily expand the questions or observations outside of their defined protocols for a particular procedure without requiring additional customization of the available exam protocols.

In addition, the user interface can be tailored to the diagnostic imaging procedure to be undertaken. The manner of this tailoring can be determined at least in part by analyzing the typical workflow involved in performing the diagnostic imaging procedure and then categorizing the elements of that workflow into a hierarchy, e.g., a planned user interface hierarchy for an application, such as obstetrics (OB), gynecological (GYN) and breast exams. This hierarchy can be based on interrelationships of the various workflow elements and based on frequency of each workflow element actually being addressed during the procedure.

For example, in the case of ultrasound OB examination, the hierarchy can be as follows:

Primary questions under category of PLACENTA:
Longitudinal Position, Transverse Position, Appearance, Cord Vessels, Grade, Chorionicity
Primary questions under category of FETAL POSITION:
Presentation, Head, Spine, Gestational Location, Yolk SAC, Probes Used
Primary questions under category of FETAL HEART:
4 Chamber View
>Secondary questions under category of 4 CMBR VIEW (B-Mode and Color Doppler):
Atrial Chambers, Interatrial Septum, Foramen Ovale, Lt. Pulmonary Veins, Rt. Pulmonary Veins, Ventricular Chambers, Interventricular Septum, Mitral Valve, Tricuspid Valve, Mitral/Tricusp Valve Insert (Color Doppler N/A), Papillary Muscle RV (Color Doppler N/A), Papillary Muscle LV (Color Doppler N/A), Rt. Pericardium, Lt. Pericardium
Location/Size
>Secondary questions under category of LOC/SZ (B-Mode):
Heart Location in Chest, Size of Heart, Cardiac Situs, Heart Axis in Degrees (B-Mode N/A)

Rhythm
Lt. Outflow Tract
  >Secondary questions under category of LT OUTFLOW TRACT (B-Mode and Color Doppler):
    Ascending Aorta, Aortic Arch, Thoracic Aorta
Rt. Outflow Tract
  >Secondary questions under category of RT OUTFLOW TRACT (B-Mode and Color Doppler):
    Main Pulmonary Artery, Ductus Arteriosis, Rt. Pulmonary Artery, Lt. Pulmonary Artery
Venous System
  >Secondary questions under category of VENOUS SYSTEM (B-Mode and Color Doppler):
    Inferior Vena Cava, Superior Vena Cava, Ductus Venosis, Mid Hepatic Veins, Lt. Hepatic Veins, Rt. Hepatic Veins
Primary questions under category of FETAL ANATOMY:
Gender
Intracranial
  >Secondary questions under category of INTRACRANIAL:
    Lat Ventricles
      Tertiary questions under category of LAT VENT:
        Anterior Horn, Posterior Horn, Inferior Horn
    Third Ventricle
    Third Ventricle Length
    Fourth Ventricle
    Choroid Plexus
    Thalami
    Corpus Callosum
      Tertiary questions under CORPUS CALLOSUM:
        Beak, Knee, Body, Tail, Pericallosal Artery Corpus Callosum Thickness
    Cava
      Tertiary questions under CAVA:
        Septi Pellucidi, Vergae, Lateral Walls, Midline
      Tertiary questions under category of MIDLINE:
    Midline
      Falx
    Cerebellum
    Cerebellum Biometry
    Cisterna Magna
    Cisterna Magna Biometry
    Parenchyma
      Tertiary questions under PARENCHYMA:
        Giri/Sulci
        Giri/Sulci Median Plane
        Giri/Sulci Coronal Plane
    Parenchyma Location
    Arteries/Veins
      Tertiary questions under ARTERIES/VEINS:
        Carotid Arteries
        Anterior Cerebral Artery
        Pericallosal Artery
        Vein of Galen
        Rt. Mid Cerebral Artery
        Lt. Mid Cerebral Artery
    Custom Question
    Outer Binocular Distance
    Ventricular Atrium Measurement
Facial
  >Secondary questions under category of FACIAL:
    Orbits
    Outer Binocular Distance
    Inner Binocular Distance
    Palate
    Maxilla
    Maxilla Biometry
    Mandible
    Mandible Biometry
    Lips
    Nasal Bone
    Nasal Bone Biometry
    Nostrils
    Ear
    Ear Length
    Neck
Thoracic Circumstances
Spine
  >Secondary question under category SPINE:
    Cervical
    Thoracic
    Lumbar
    Sacrum
    Coccyx
Upper Extremity
  >Secondary question under category UPPER EXTREMITY:
    Arms
    Hands
    Fingers
    Humerus Biometry
    Ulna Biometry
    Radius Biometry
Lower Extremity
  >Secondary question under category LOWER EXTREMITY:
    Legs
    Feet
    Toes
    Tibia
    Foot
    Fibula
Abdominal Wall
Abdominal Cavity
Stomach Fluid
  >Secondary question under category STOMACH FLUID:
    Stomach Biometry
Bladder Fluid
  >Secondary question under category BLADDER FLUID:
    Bladder Biometry
Rt. Kidney
  >Secondary question under category RT. KIDNEY:
    Kidney Biometry
Lt. Kidney
  >Secondary question under category LT. KIDNEY:
    Kidney Biometry
Primary questions under category of MATERNAL ANATOMY:
  >Secondary questions under MATERNAL ANATOMY:
    Kidneys
    Uterus
    Cul-de-sac
    Rt. Ovary
    Lt. Ovary
    Adnexa
    Type of finding
    HCG
    Serum HCG
    Endometrial Stripe
    Endometrial Stripe Biometry Cervix
>Secondary questions under category CERVIX:
  Pessary
  Cerclage
  Beaking
  Funneling
  Prolapse
  Funnel Width
  Funnel Length
  Closed Canal Length
  Cervix Length
Cervix Length
Primary questions under category AMNIOTIC FLUID:
AFI
Deepest Pool (MVP)
Findings
  >Secondary questions under category PULSED DOPPLER:
    Rt. Uterine
    Rt. Uterine Biometry
    Lt. Uterine
    Lt. Uterine Biometry
    Middle Cerebral
    Middle Cerebral Biometry
    Umbilical
    Umbilical Biometry
    Fetal Aorta
    Fetal Aorta Biometry
  >Secondary questions under category AMNIOCENTESIS:
    Amniocentesis
    Location
    Attempts
    Purpose
    Approach
    Post Amnio Fetal Heart
    Fluid Appearance
    Rhogam
    Maternal Blood Type
    Estimated Volume
  >Secondary questions under BIOPHYSICAL PROFILE:
    Fetal Movement
    Fetal Tone
    Fetal Breathing
    Amniotic Fluid Volume
    Reactive Heart Rate
    Custom Question
  >Secondary questions under category CVS:
    Location
    Attempts
    Purpose
    Approach
    Post CVS Fetal Heart
    RH
    Rhogam
    Maternal Blood Type
    Estimated Weight
  >Secondary questions under category NST:
    NST
    Baseline FHR
    Decelerations
    Decel Type
    Contractions
    Movement
    Custom Question
  >Secondary questions under category CUSTOM SECTIONS:
    30 Customizable Headers
    180 Customizable Questions
    180 Customizable Pick List Options
  >Secondary questions under category DEMOGRAPHICS:
    Procedure Codes
    LMP/DOC/EDD
    Gravida
    Para
    Study Date & Number
    Gestation
    Baby
    Accession #
    UID
    Referring Provider
    Indications
    Fees & Collections
  >Secondary questions under category COMMENTS:
    Comments
    Diagnosis Codes
    Follow-UP The available responses for each of the questions above can come from a basic set of the generally used responses, but can also be fully customizable. For an example of the above hierarchy represented in a user interface page, see FIG. 6. In this fashion, Rapid Reports removes the confines created by the traditional approach to procedure documentation and introduces an electronic documentation process more in line with how people think. Moreover, this tailoring of the user interface can be extended to additional reconfigurations of the user interface for different types of exams performed within one general application category, such as ultrasound OB exams.

Figure 2:
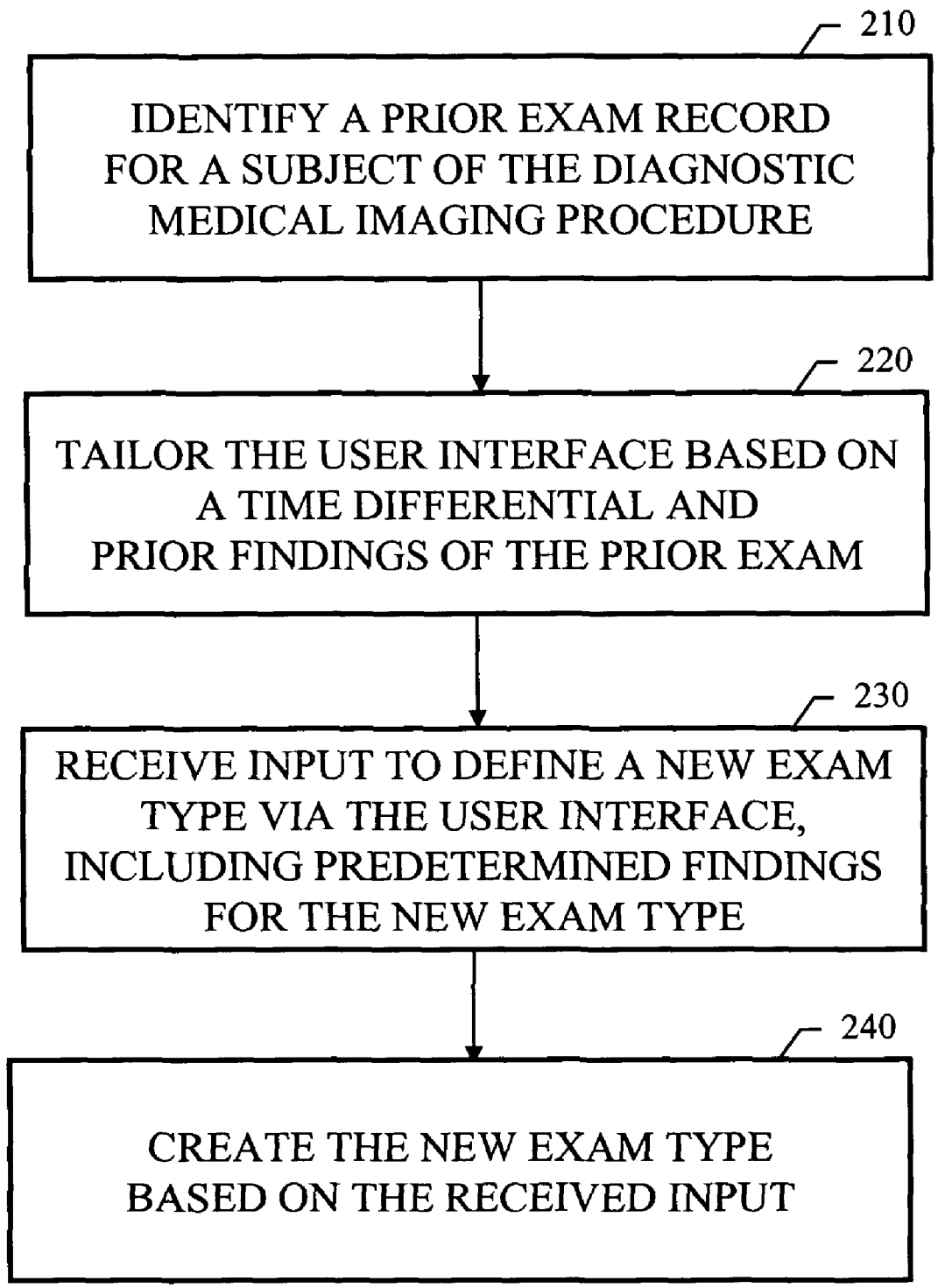
FIG. 2 shows operations of a process of reconfiguring a user interface used in documenting a diagnostic medical imaging procedure.

FIG. 2 shows operations of a process of reconfiguring a user interface used in documenting a diagnostic medical imaging procedure. A prior exam record for a subject of the diagnostic medical imaging procedure can be identified at 210. This can involve pulling one or more exam records from local storage or from a remote server. The user interface to be presented can then be tailored to a new exam based on a time differential between the prior exam(s) and the diagnostic medical imaging procedure being conducted, and based on prior findings of the prior exam(s), at 220.

Moreover, the user interface and the defined clinical protocols can be customized through the graphical user interface of the program. Input can be received at 230 to define a new exam type via the user interface, including predetermined findings for the new exam type. The new exam type can be created based on the received input at 240. Thus, end-users can incorporate their own practice protocols to meet their practice goals with minimal computer literacy or prior experience.

The above described features are now described in detail in the context of an ultrasound OB exam implementation. A patient can be scanned on an ultrasound machine that uses the Rapid Reports program or that is connected to a data processing apparatus that uses the Rapid Reports program. After completing the exam on the ultrasound machine, the sonographer can transfer the data to Rapid Reports at the push of a button if the program is connected to the ultrasound machine, or the data already present if Rapid Reports resides in the ultrasound machine. The user can then select among initial user interface options to specify the input screen for a patient not previously scanned (e.g., the options can include Complete Report, First Trimester Report, 14-20 Wks Report, 20+

Wks Report, and Antepartum Report). If the user selects first trimester for the current patient, the program configures the user interface to present a first trimester user interface window.

Figures 3, 4:
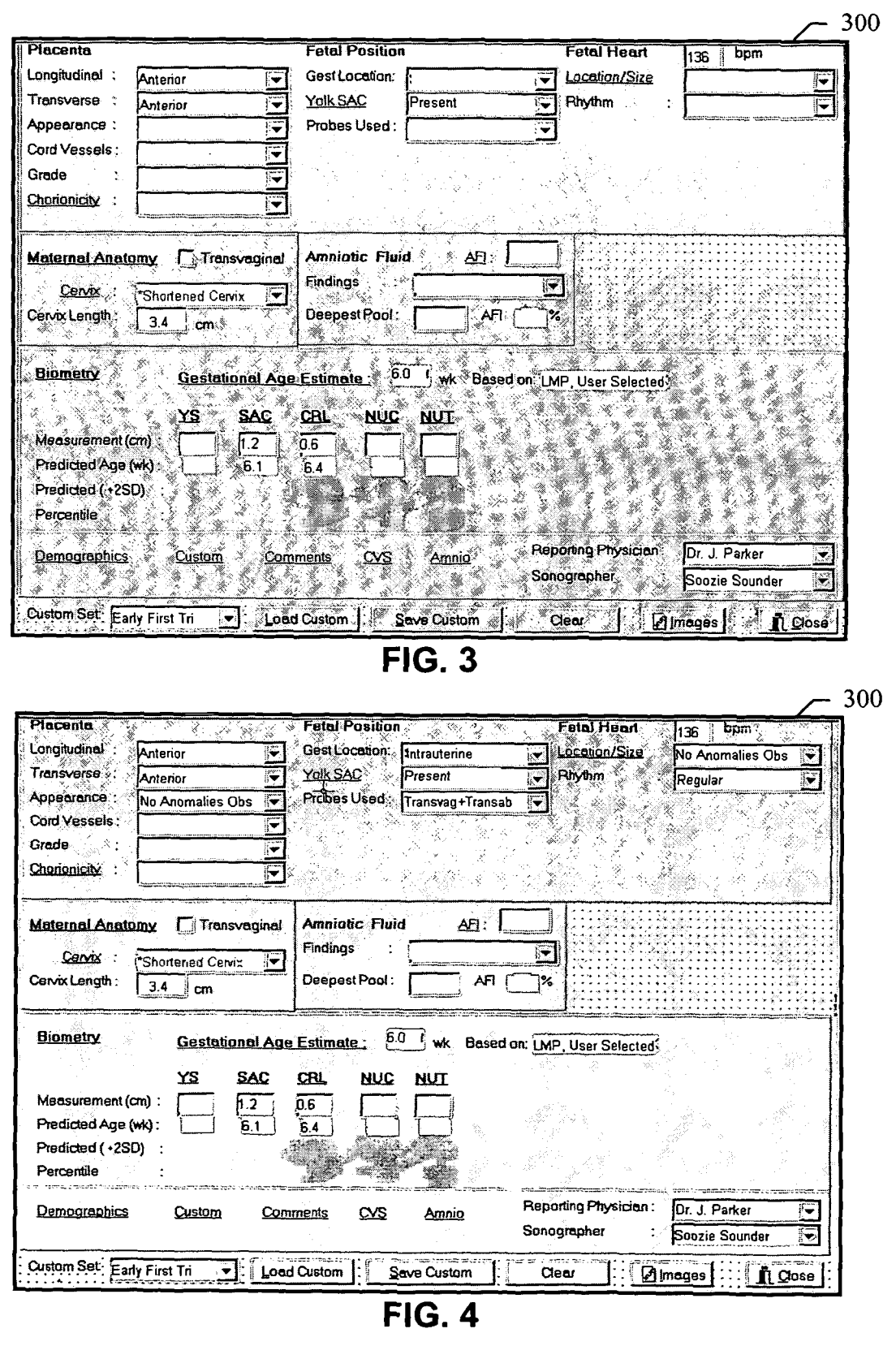

FIG. 3 shows an early first trimester user interface window 300 after selection of items considered an exception or difficult to anticipate as part of a protocol. These items can include Longitudinal and Transverse Placenta, Yolk SAC and a Shortened Cervix Anomaly. Any item that can be considered to be an item of concern (in this case the Shortened Cervix Anomaly) can be displayed in red, or otherwise set off to make it easier to notice in the interface. The Biometry for Fetal Heart, Cervical Length, SAC and CRL can come directly from the ultrasound machine. Reporting physician and sonographer can be a default as part of the system configuration, from the Hospital Information System or the Ultrasound Machine. The total number of clicks to complete the drop down box selections on this window/page can thus be four.

Once items considered to be exceptions are responded to, the user can select the appropriate protocol, in this case "Early First Trimester", which defines a set of global expected responses for the predefined exam procedure, then the user can click "Load Custom" to load the custom global responses. All appropriate remaining fields according to the user's defined protocol are filled in, including any of the pop-ups found when clicking on underlined items in the interface window 300. This study can then establish a benchmark for the user interface on the follow-up study. FIG. 4 shows the early first trimester user interface window 300 of FIG. 3 after user-defined custom responses have been loaded.

FIG. 5 shows a report 500 generated for the early first trimester exam by the Rapid Reports program. In this example, the full documentation and reporting process required approximately fifteen seconds to complete and provides a benchmark for the user interface in the follow-up exam. The follow-up exam's user interface can be automatically generated as determined by information gathered during the initial exam, including GA. The initial exam determined the GA of the Fetus to be 6 weeks. When approximately 14.5 weeks have elapsed between the initial exam and the follow up exam, the Rapid Reports program automatically calculates the new expected GA to bring up a 20+ week interface.

Figure 6:
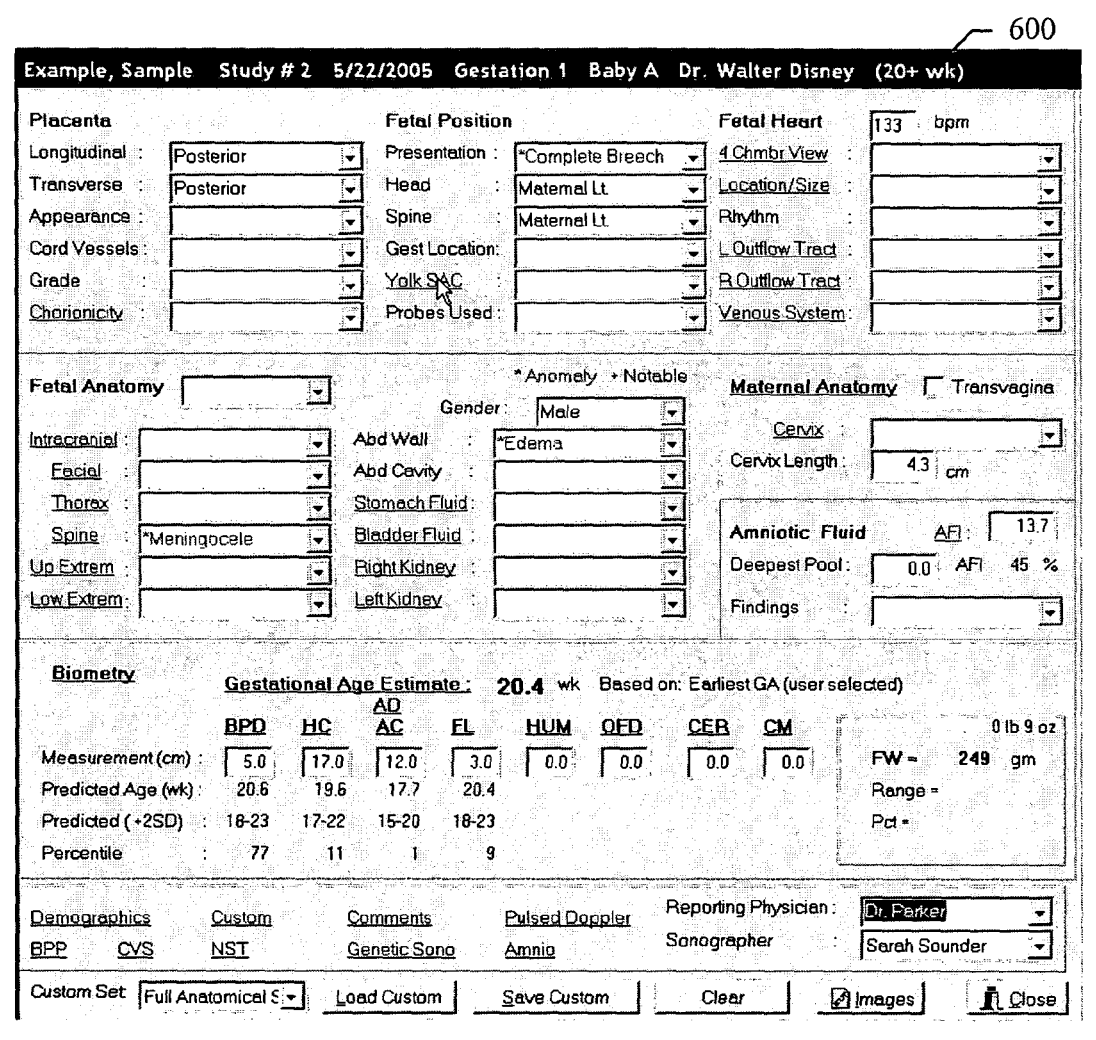

FIG. 6 shows a 20+ weeks ultrasound exam user interface window 600 after selection of items considered an exception or difficult to anticipate as part of an anatomical survey. These items can include Longitudinal and Transverse Placenta, Fetal Position Questions, Gender, two Anatomical Anomalies (Meningocele and Edema) and a poorly seen Interatrial Septum. Again, all biometry can be automatically loaded directly from the ultrasound machine, and the reporting physician and sonographer can be a default. The total number of clicks to complete this page can thus be ten.

Figure 7:
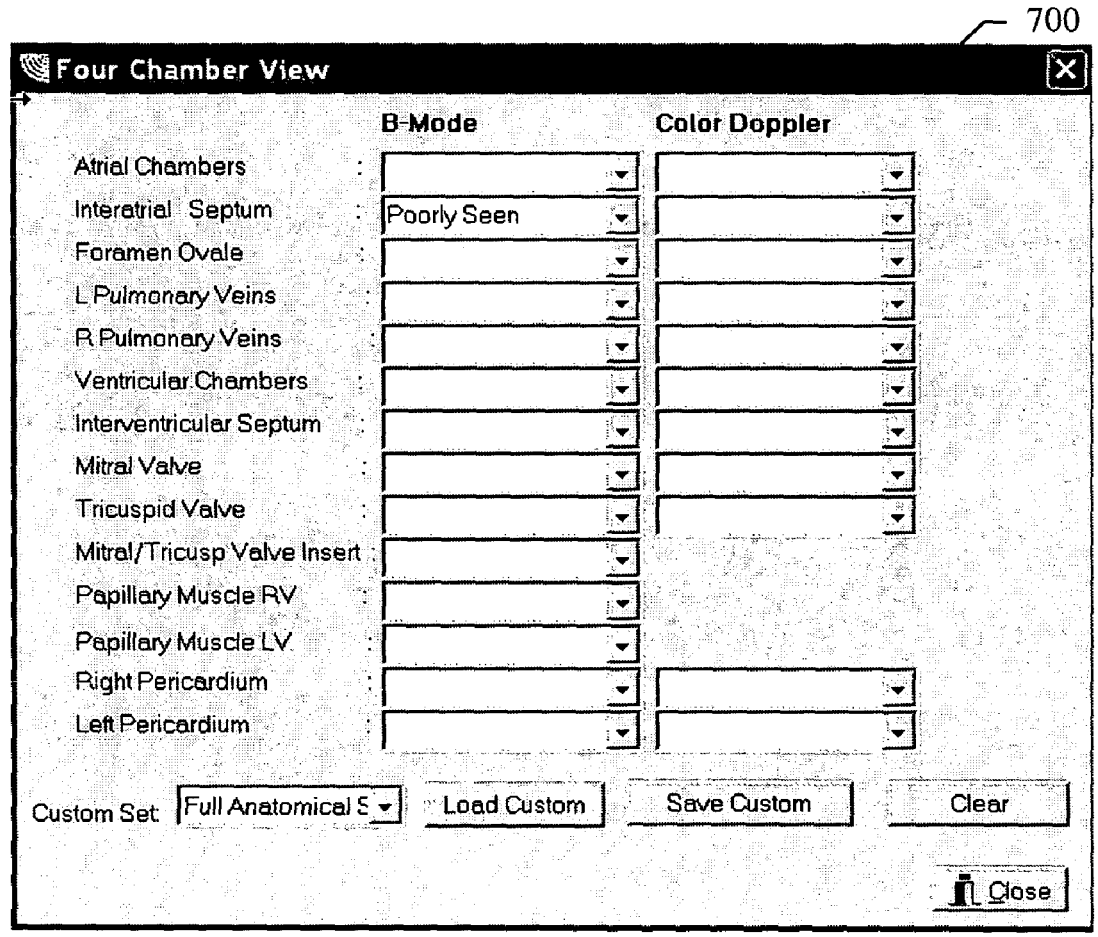
FIG. 7 shows a pop-up dialog window triggered by selection of the 4 Chmbr View field in FIG. 6.

The total of ten clicks includes three clicks for drilling down to the secondary questions on 4 Chamber View. Clicking on the 4 Chmbr View link in the window 600 causes a pop-up dialog window to open in this example user interface. FIG. 7 shows the pop-up dialog window 700 triggered by selection of the 4 Chmbr View field in FIG. 6. The "Poorly Seen" option is selected for "Interatrial Septum" with a second click, and the window 700 is closed with a third click. This drilling down to the secondary question can now be reflected in the main window 700, such as by changing the color of the 4 Chmbr View link (e.g., from green to blue to indicate a selection of the link has occurred). Thus, the main page can summarize findings information documented in the user interface through one or more drill down actions, allowing a user to keep track of what portions of a diagnostic imaging procedure have been completed.

Figure 9A:
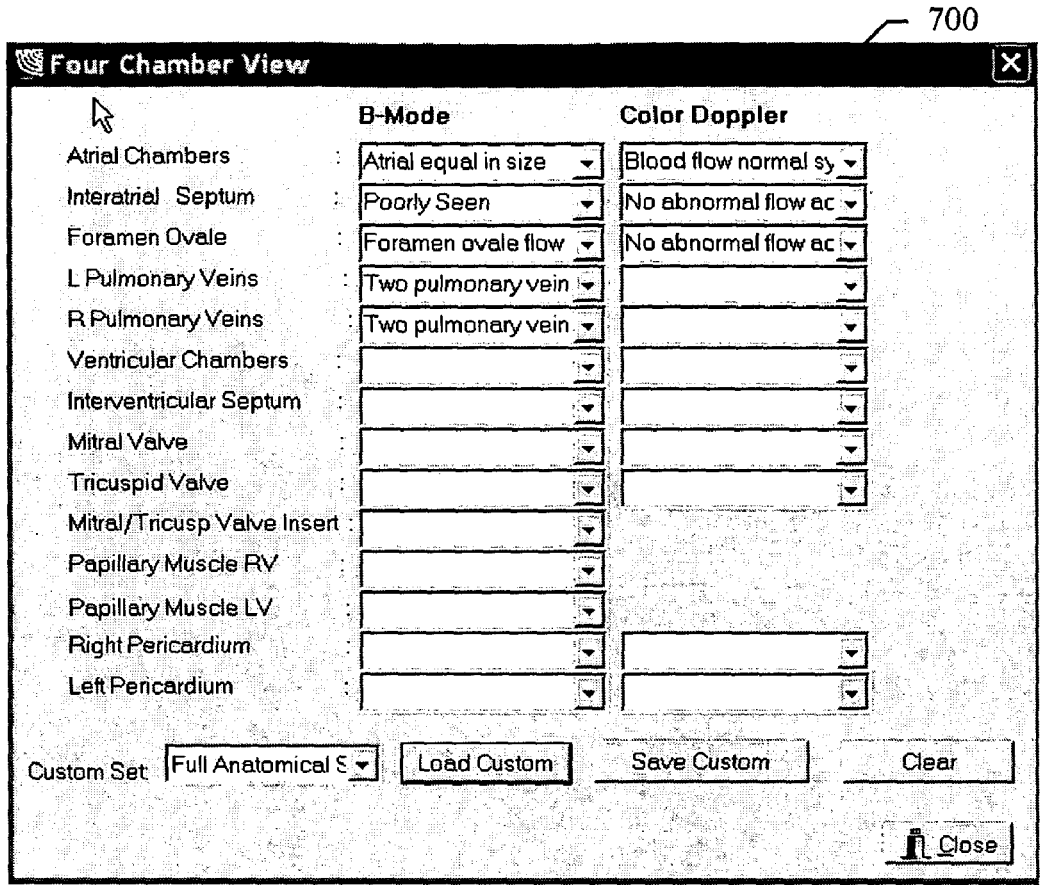
Figure 9B:
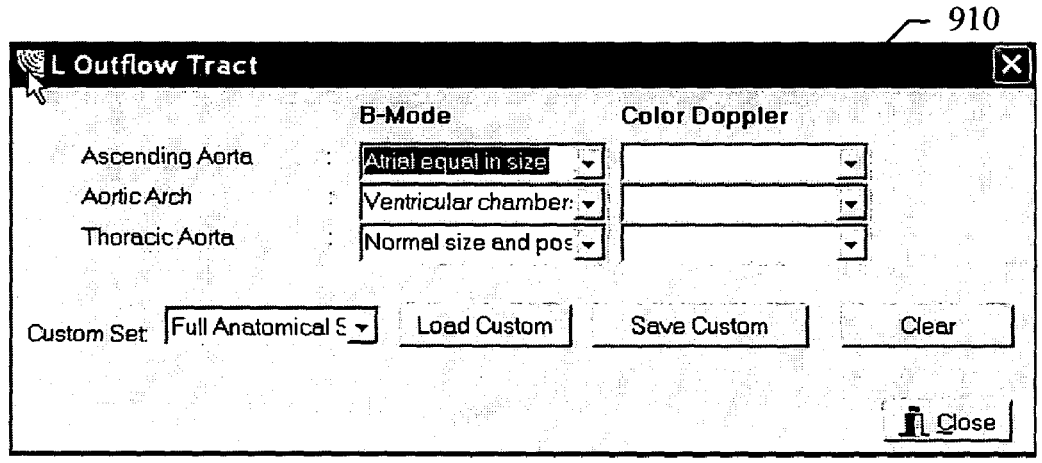
Figures 9C, 9D, 9E:
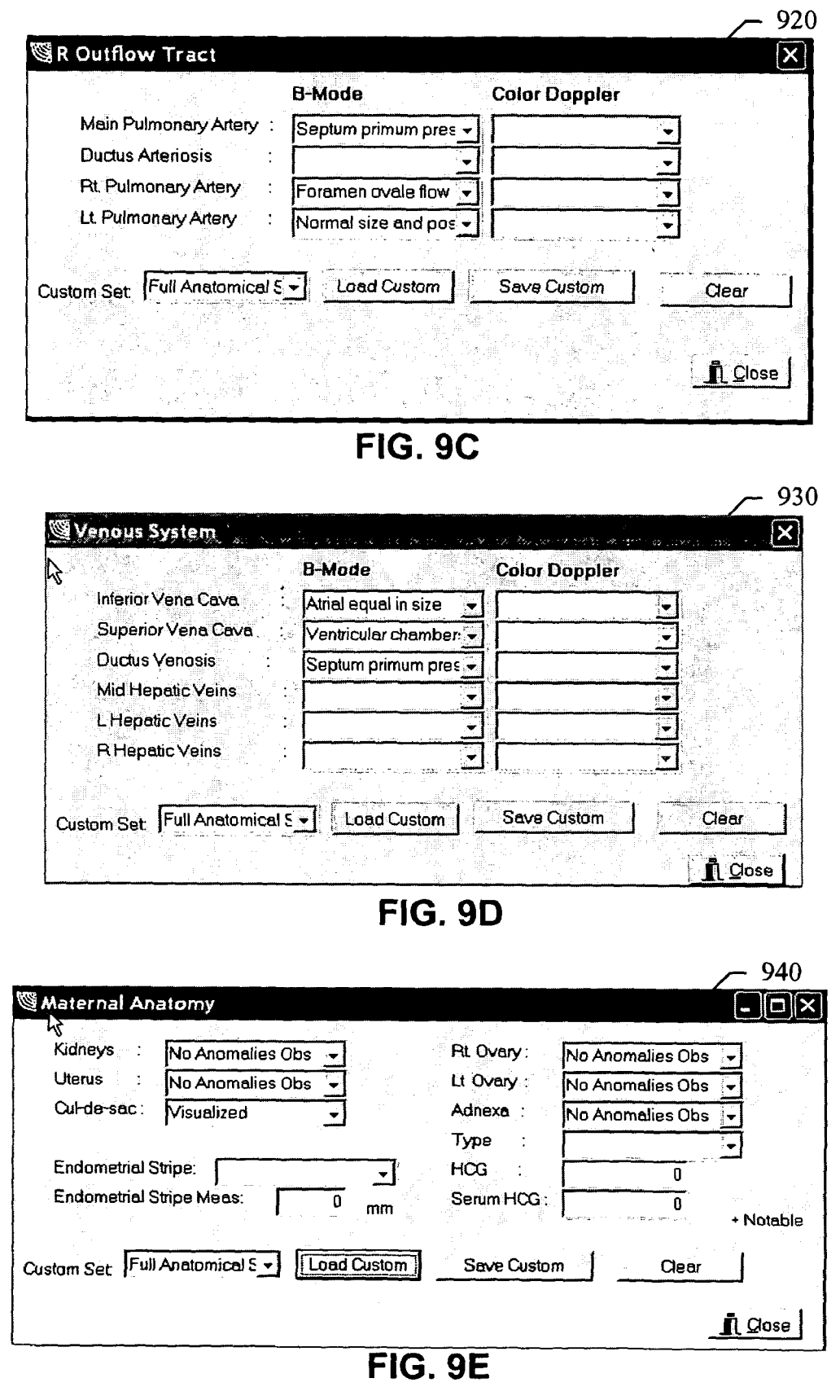
Figures 9F, 9G:
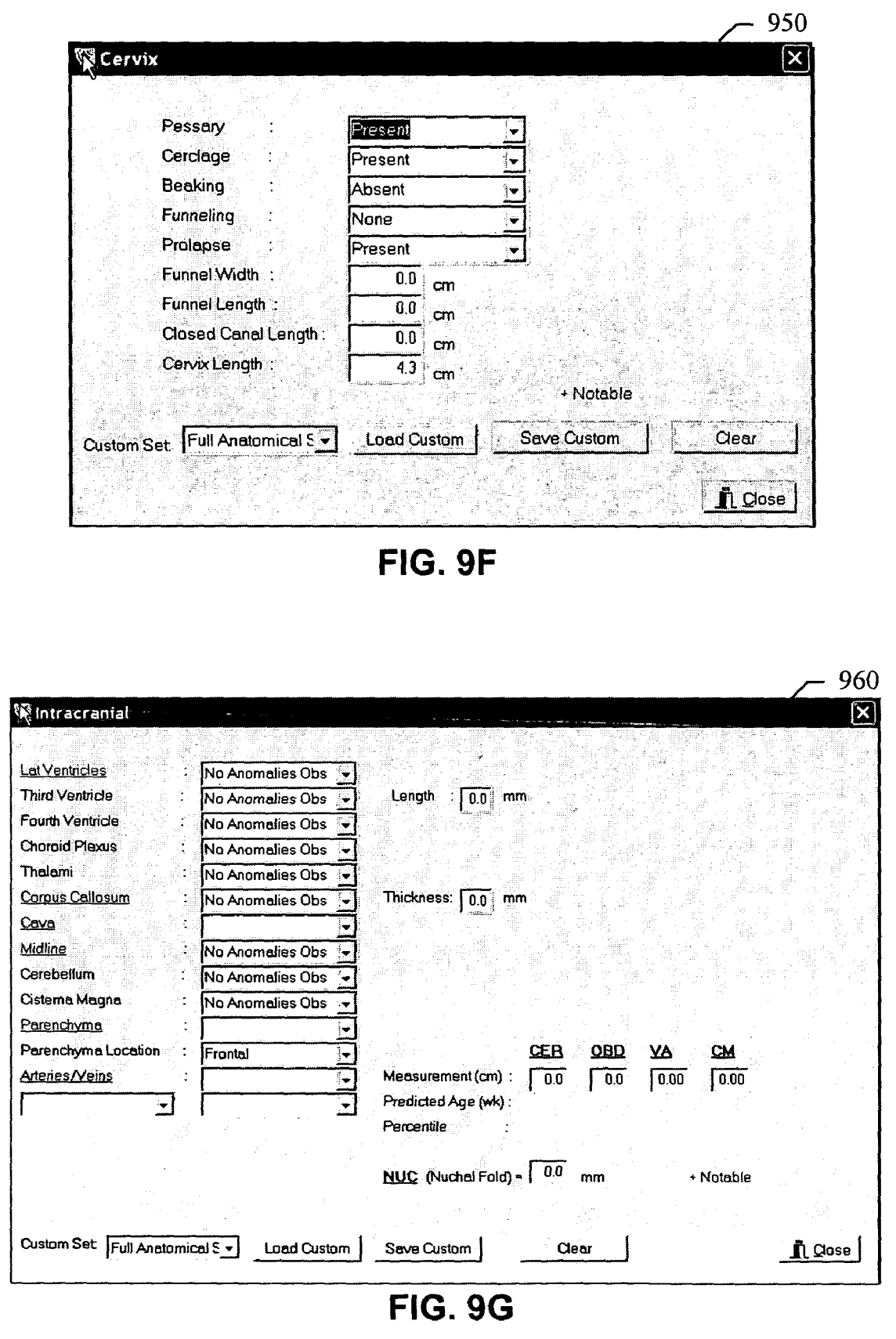
Figures 9H, 9I, 9J:
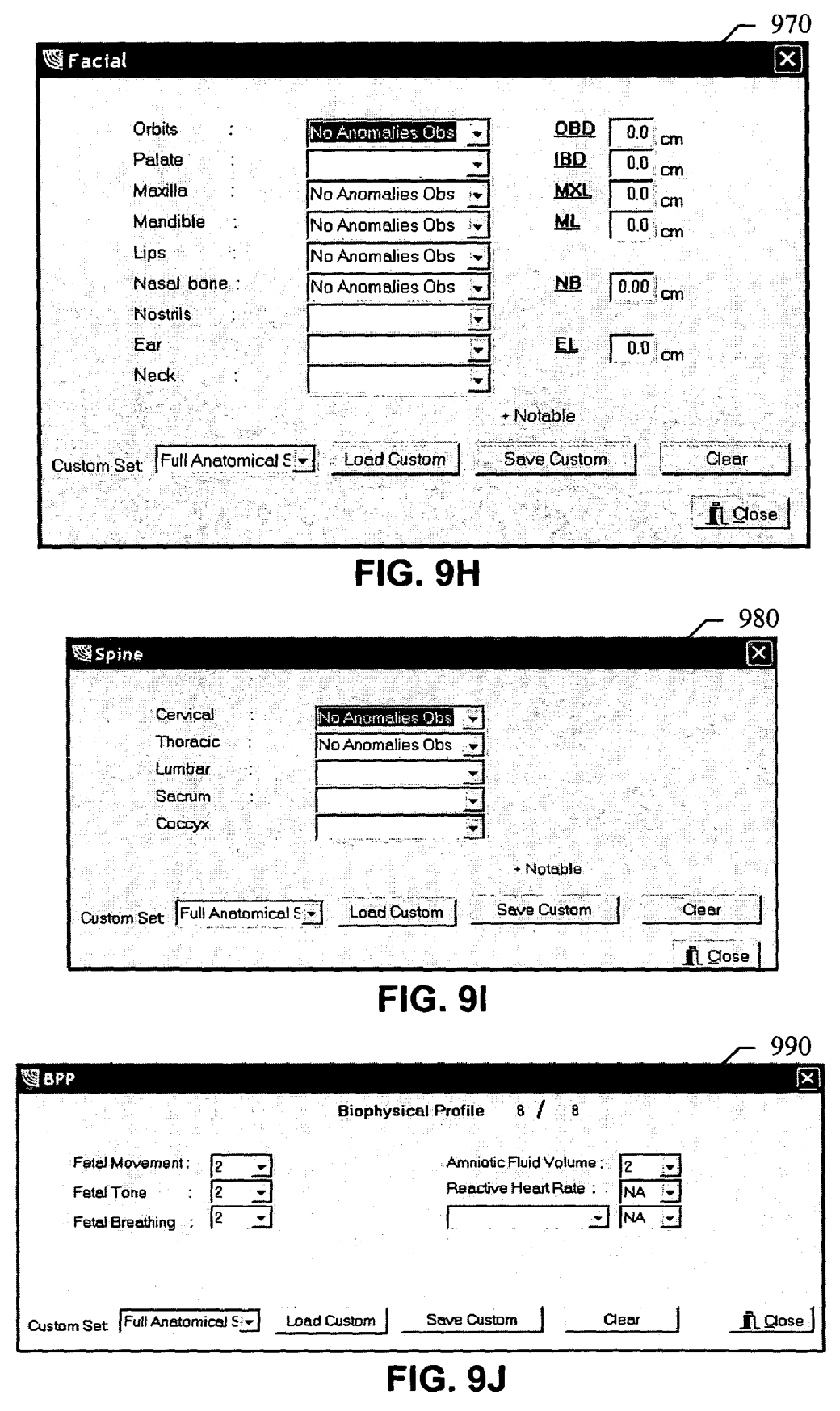

FIG. 8 shows the 20+ weeks ultrasound exam user interface window 600 after user-defined custom responses have been loaded for a full anatomical survey protocol. These custom responses include responses to all appropriate fields, and the user can be prompted as to whether loading of custom responses should be limited to the current window, limited to the current window and all subsidiary windows, or be applied to all available windows. In the latter two cases, loading custom responses in the main window results in automatic loading of the custom responses in the fields located in all subsidiary windows, even when those windows are not open at the time. For example, if the 4 Chmbr View link were to be clicked again after loading all the custom responses from the main window, all the additional fields specified as checked in the loaded protocol will also be filled in. FIG. 9A shows the pop-up dialog window 700 triggered by selection of the 4 Chmbr View field in FIG. 8. FIGS. 9B-9J show various additional pop-up dialog windows 910, 920, 930, 940, 950, 960, 970, 980 and 990 triggered by selection of elements in FIG. 8. As shown, the custom global responses here can be tailored to the end-user's own definition of a full anatomical survey. Moreover, all these customized responses can be automatically loaded without requiring any user interaction with (or even opening of) the pop-up dialog windows 910, 920, 930, 940, 950, 960, 970, 980 and 990.

Figure 11:
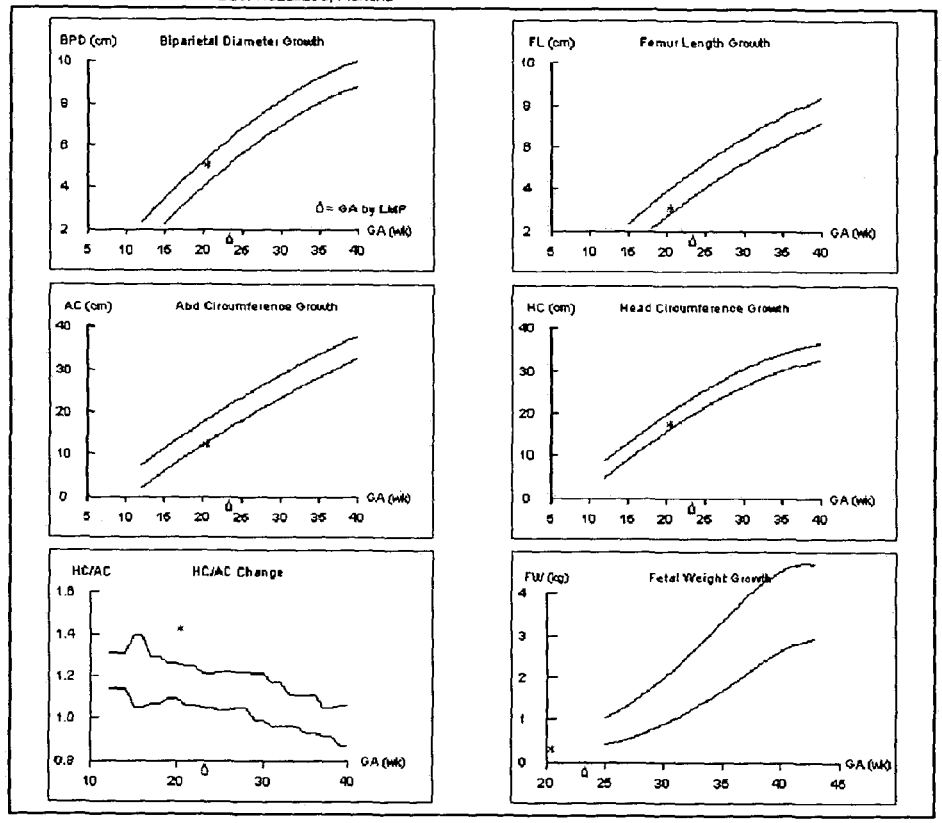

FIGS. 10 and 11 show a report 1000 generated for the 20+ weeks full anatomical survey protocol. In this example, the full documentation and reporting process required approximately twenty seconds to complete and provides a benchmark for the user interface in the follow-up exam.

Figure 12:
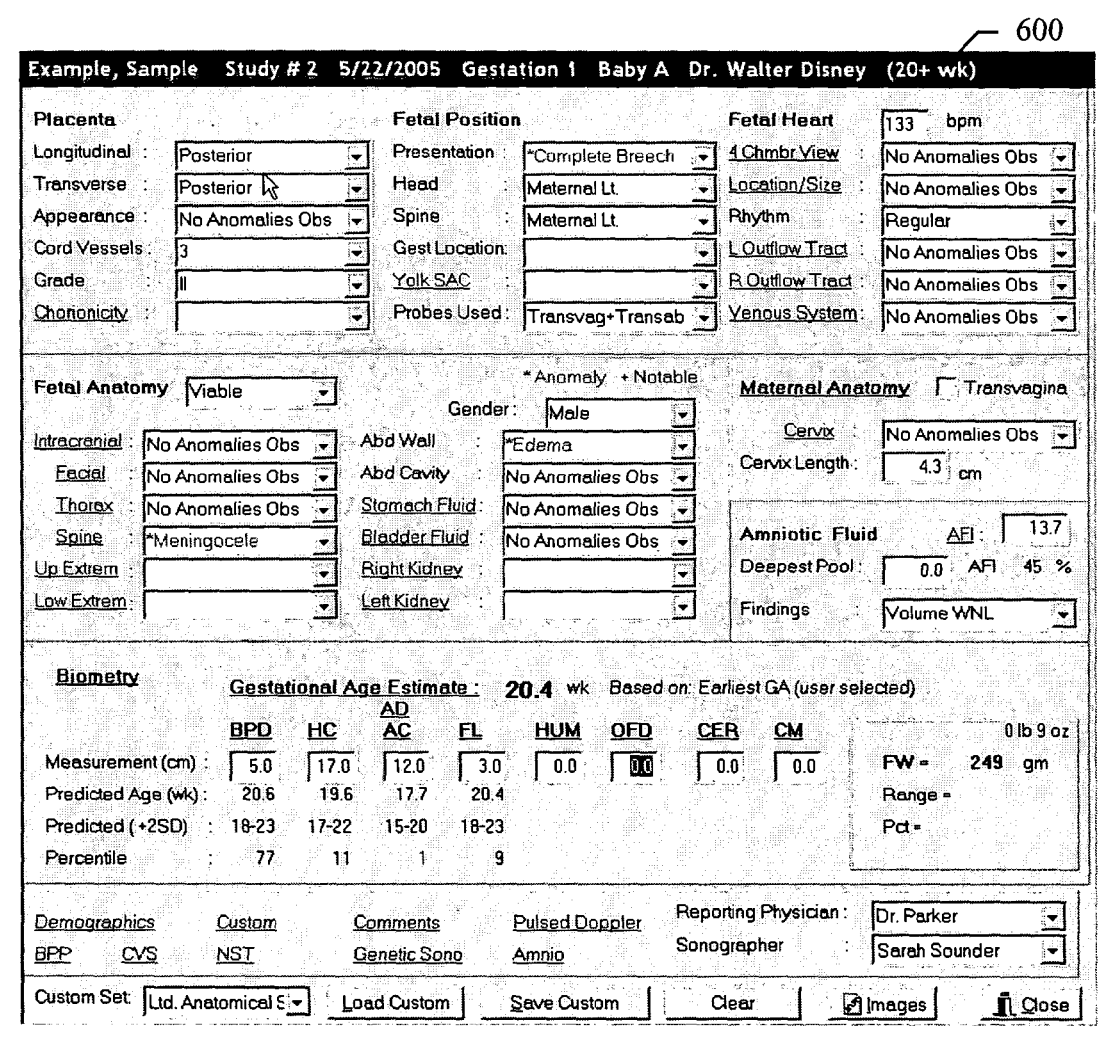

However, during this second exam, the patient may not need a Full Anatomical Survey but instead the patient may only require a Limited Anatomical Survey. The difference between performing a Full Anatomical Survey and a Limited Anatomical Survey would be to select a different protocol, as findings considered to be an exception would still be documented in both protocols. FIG. 12 reflects a user selecting a Limited Anatomical Survey instead of the Full Anatomical Survey. The amount of time and the number of clicks to complete either report is the same.

FIG. 12 shows the 20+ weeks ultrasound exam user interface window 600 after user-defined custom responses have been loaded for a limited anatomical survey protocol. Note that many of the fields loaded in FIG. 8 are not done so in FIG. 12. The protocols defined by users can have the flexibility to be expanded or contracted during the exam to enable users to alter the direction of an exam as additional information is discovered.

Figure 14:
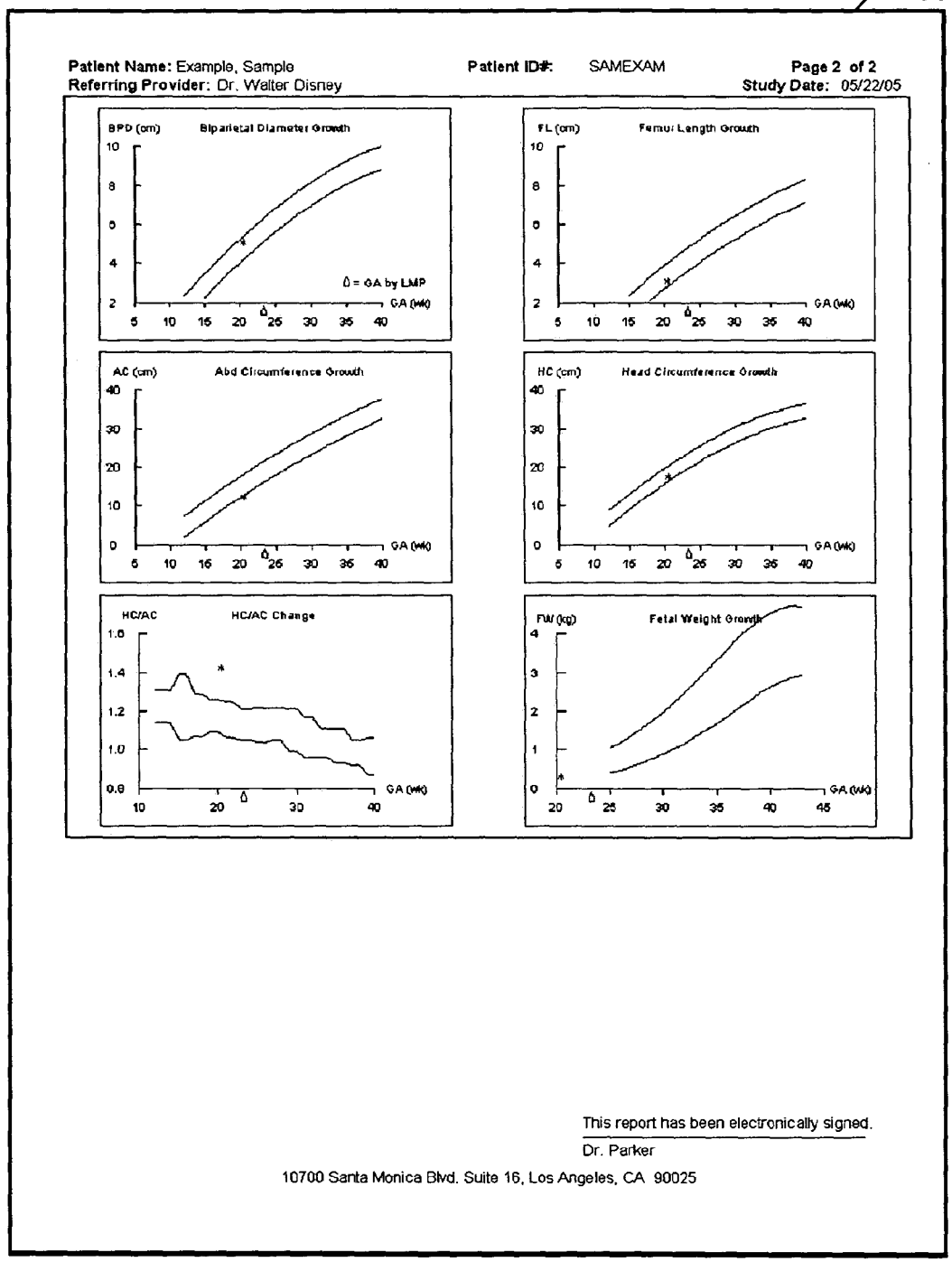

FIGS. 13 and 14 show a report 1300 generated for the 20+ weeks limited anatomical survey protocol. Note the difference between the Limited Anatomical Survey Report 1300 and the Full Anatomical Survey Report 1000. While both reports are materially different they generally require the same number of clicks as well as the same amount of time to generate. As this example shows, there is no need to flip through a bunch of pages to document the exam, or go to a separate report page before generating a full report of the exam, regardless of the type of report being generated.

Figure 15:
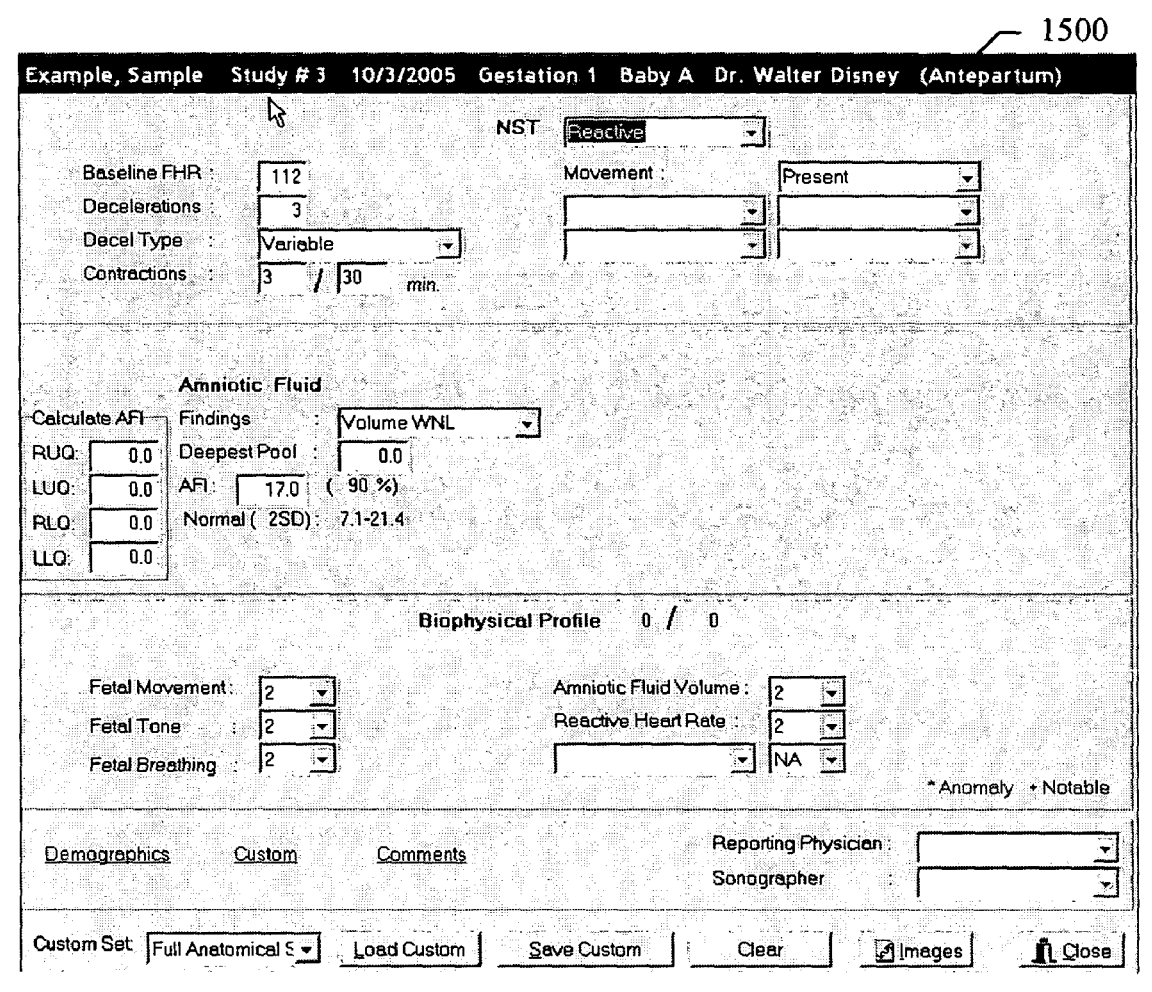

Approximately 19 weeks after the second exam, the same patient comes back for a third exam, and the Rapid Reports program automatically adjusts the user interface to support an Antepartuth exam based on the time difference and the determined GA from the second exam. FIG. 15 shows an antepartum ultrasound exam user interface window 1500 generated approximately nineteen weeks later. Note how the antepartum interface allows for a more targeted user interface experience.

Figure 16:
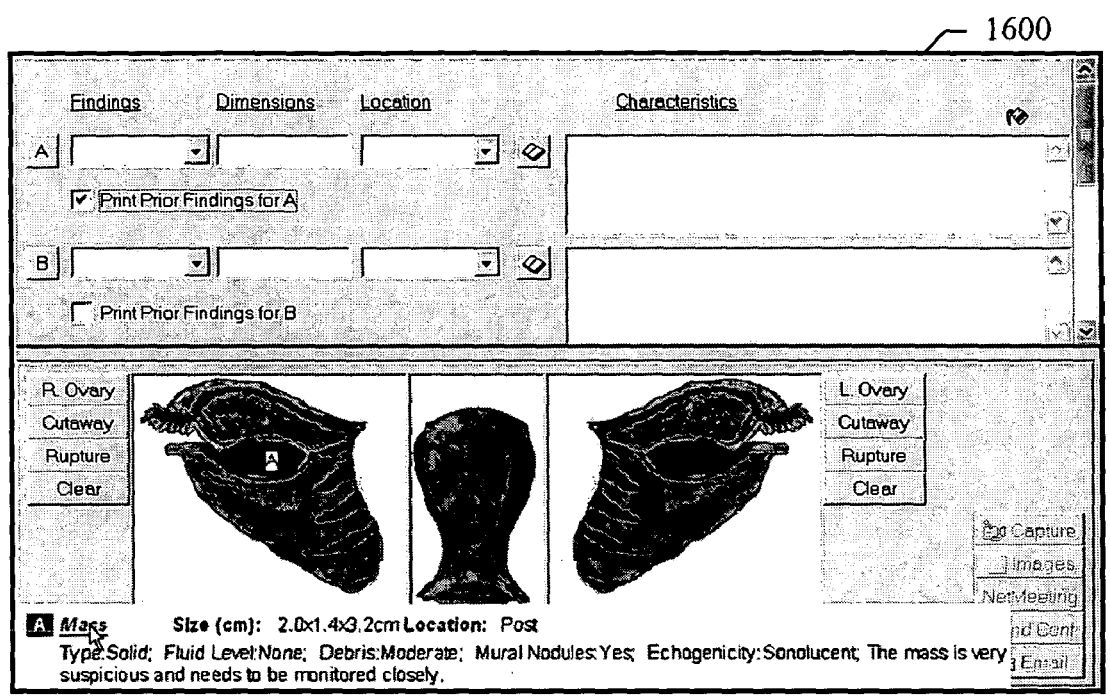
FIG. 16 shows an example user interface window for a gynecological exam.

Another example of the Rapid Reports program streamlining the documentation of an exam to allow for point of service implementation is now illustrated by a GYN example. FIG. 16 shows an example user interface window 1600 for a gynecological exam. In this example, a mass identified by a prior exam is used to manage the current exam being performed. Incorporating observations and findings from earlier exams as part of the user interface, can be used to influence the user interface of a program and materially improve the clinical management of an exam. The user can then review the finding of the prior exam, document any changes observed during the current exam, then at the click of a button bring forward the findings of the prior exam without overwriting the new findings entered. This can save users a substantial amount of time. The GYN example here shows the prior finding of a GYN exam, which guides the user to perform a more complete exam and not overlook prior data. This can thus positively influence the current exam being performed.

Importing and integrating findings from modalities different than the modality used to perform the exam can also improve the clinical management of the exam. The Rapid Reports program can include the ability to integrate multiple exam reports into a contiguous information stream. For example, with a breast exam one can have up to five independent providers performing an exam. One can have the primary OB performing the manual breast exam, the radiologist performing the mammogram, an ultrasound specialist performing the breast ultrasound exam, the surgeon performing the fine needle aspiration, and the pathology department performing the analysis of the fine needle aspiration. In traditional approaches to this workflow, the communication among these five independent providers is often poor and rarely does the data from the prior exam follow over to the next provider. Thus, the benefit of the preceding exam data may be lost, potentially resulting in a reduced benefit from the follow-up exam.

With regards to breastwork, usually a breast physical exam will be the event that triggers a mammogram. The triggering information can then carry over to the mammogram report. The mammogram may trigger either a breast ultrasound or a fine needle aspiration. The triggering event of the mammogram (as well as the triggering event that caused the mammogram) can then follow over to the practitioner performing the breast ultrasound or fine needle aspiration. This type of electronic audit trail can be maintained by the Rapid Reports program, enabling any practitioner in the chain to readily pull up and, if appropriate, integrate prior reports during a current exam and providing a very efficient workflow.

Figure 17:
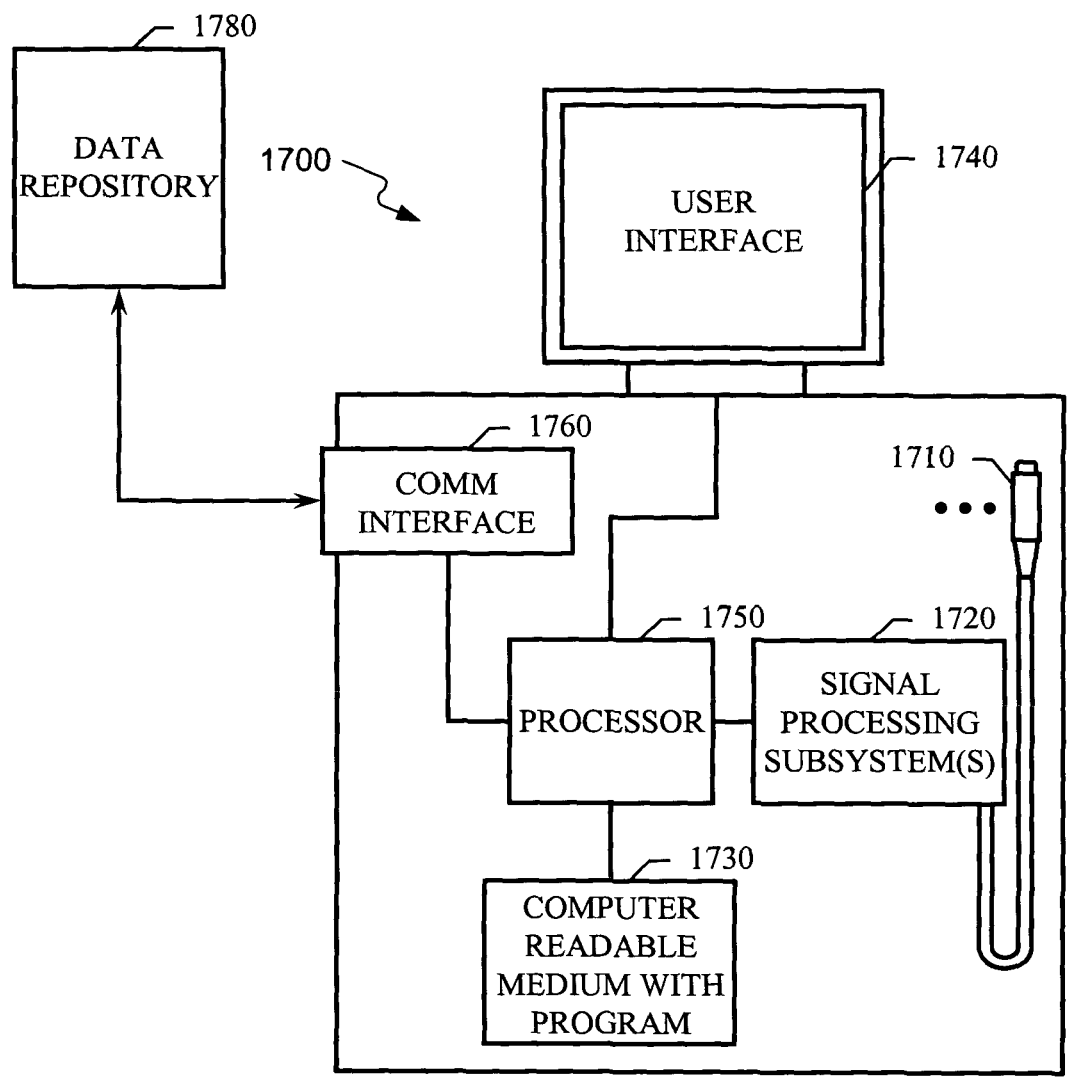
FIG. 17 shows an ultrasound imaging system.

FIG. 17 shows an ultrasound imaging system 1700. The system 1700 includes one or more ultrasound transducer probes 1710 coupled with one or more signal processing subsystems 1720. The system 1700 also includes a computer-readable medium 1730 including encoded thereon a program operable to cause the ultrasound imaging system 1700 to present a user interface 1740 that enables documentation by exception of an ultrasound exam. The user interface 1740 can provide access to prior exam findings and can be configured at least in part based on the prior exam findings (e.g., at least in part based on a change in the prior exam findings). Moreover, the program can generate an electronic report including the documentation of the ultrasound exam, and potentially also including the prior exam findings; including the prior exam findings can occur in response to an indication of clinical relevance of the prior exam findings, which indication can come from user input or be a preprogrammed indication for the type of exam performed.

The documentation can include both exam findings and pertinent negatives, where the exam findings are received through the user interface 1740, and the pertinent negatives are automatically loaded in response to an exam type selection made during performance of the ultrasound exam but after receipt of at least some of the exam findings. The prior exam findings can include information retrieved from a data repository 1780 (e.g., a server) through a communications interface 1760. The prior exam findings can include information regarding a prior, non-ultrasound exam.

The program on the computer-readable medium 1730 can be executed using a processor 1750 and can reside within an ultrasound machine or reside in another machine connected to an ultrasound machine. Thus, the system 1700 can be a single ultrasound machine or an ultrasound machine with a data processing machine (e.g., a personal computer) attached. Typically, ultrasound machines are expensive pieces of medical equipment that need to have a high utilization rate to justify their cost. However, the Rapid Reports program is efficient enough to justify including the documentation and reporting process on the ultrasound machine itself. The Rapid Reports program can be designed to import data (biometric and imaging data) from other pieces of medical equipment, including equipment from various manufacturers. Moreover, the same program can reside on an ultrasound scanner as well as on a separate computer, and the two instances of the program can share data and database(s). Data can be shared in either direction (uploaded or downloaded) to optimize productivity. This may help when a physician scans first on one scanner, such as an HDI 5000, and then wants to complete the exam on another scanner, such as a Voluson 730.

The systems and techniques and all of the functional operations described in this specification can be implemented in digital electronic circuitry, or in computer software, firmware, or hardware, including the structural means disclosed in this specification and their structural equivalents, or in combinations of them. Embodiments of the invention can be implemented as one or more computer program products, i.e., one or more modules of computer program instructions encoded in a computer-readable medium, e.g., a machine readable storage device, a machine readable storage medium, a memory device, or a machine-readable propagated signal, for execution by, or to control the operation of, data processing apparatus. The term "data processing apparatus" encompasses all apparatus, devices and machines for processing data, including by way of example a programmable processor, a computer, an ultrasound machine, or multiple processors or computers or ultrasound machines. The apparatus can include, in addition to hardware, code that creates an execution environment for the computer program in question, e.g., code that constitutes processor firmware, a protocol stack, a database management system, an operating system, or a combination of them. A propagated signal is an artificially generated signal, e.g., a machine-generated electrical, optical, or electromagnetic signal, that is made to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data (e.g., one or more scripts in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output.

The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, to name just a few. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball or PEN technology (e.g., a tablet computer), by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The various implementations described above have been presented by way of example only, and not limitation. For example, the logic flows depicted in the figures do not require the particular order shown, sequential order, or that all operations illustrated be performed, to achieve desirable results. In certain implementations, multitasking and parallel processing may be preferable. Also, non-medical applications of Rapid Reports are also possible. Other embodiments are within the scope of the following claims.

What is claimed is:

1. A non-transitory computer-readable medium encoding program instructions operable to cause one or more machines to perform operations comprising:

presenting a user interface that supports documentation of a plurality of medical exams available during a diagnostic medical imaging procedure;
   receiving information that specifies findings of the diagnostic medical imaging procedure via the user interface;
   receiving an exam type selection after receiving the findings information, the exam type selection corresponding to the diagnostic medical imaging procedure conducted and indicating a selected exam type from a plurality of predefined exam types; and
   loading a set of predetermined findings corresponding to the selected exam type for the diagnostic medical imaging procedure, wherein any of the predetermined findings in the set that conflict with the received findings information are disregarded.

2. The computer-readable medium of claim 1, the operations further comprising receiving additional information that specifies additional findings of the diagnostic medical imaging procedure via the user interface after loading the set of predetermined findings.

3. The computer-readable medium of claim 2, wherein the additional information specifies additional findings that change prior findings, both from the received information and from non-conflicting findings of the set of predetermined findings.

4. The computer-readable medium of claim 1, wherein the user interface comprises a single main window and one or more subsidiary windows accessible via the single main window, wherein the single main window summarizes findings information documented in the user interface, including both received specified findings and loaded predetermined findings that correspond to the one or more subsidiary windows.

5. The computer-readable medium of claim 1, the operations further comprising:
   identifying a prior exam record for a subject of the diagnostic medical imaging procedure; and
   tailoring the user interface for presentation based on a time differential between the prior exam and the diagnostic medical imaging procedure being conducted, and based on prior findings of the prior exam.

6. The computer-readable medium of claim 5, wherein the diagnostic medical imaging procedure comprises an obstetrics examination, and tailoring the user interface comprises reconfiguring the user interface for presentation in accordance with a current gestational age computed using a determined gestational age stored in the prior exam record and a difference in time between the prior exam and the obstetrics examination.

7. The computer-readable medium of claim 5, wherein identifying the prior exam record comprises identifying multiple prior examinations of the subject, and tailoring the user interface comprises reconfiguring the user interface for presentation based on a change in associated findings in the multiple prior examinations.

8. The computer-readable medium of claim 1, the operations further comprising receiving a load global response selection via the user interface, and wherein loading the set of predetermined findings occurs in response to receiving the load global response selection, and receiving the exam type selection occurs via the user interface.

9. The computer-readable medium of claim 1, wherein the exam type selection corresponds to a billing code associated with the selected exam type.

10. The computer-readable medium of claim 1, the operations further comprising:

receiving input to define a new exam type via the user interface, including predetermined findings for the new exam type; and creating the new exam type based on the received input.

11. An ultrasound imaging system comprising:

one or more signal processing subsystems;

one or more ultrasound transducer probes coupled with the one or more signal processing subsystems; and a non-transitory computer-readable medium including encoded thereon program instructions operable to cause the ultrasound imaging system to present a user interface that enables documentation by exception of an ultrasound exam, wherein the user interface provides access to prior exam findings and is configured at least in part based on the prior exam findings, and the program instructions generate an electronic report including the documentation of the ultrasound exam;

wherein the documentation includes both exam findings and pertinent negatives, the exam findings received through the user interface and the pertinent negatives automatically loaded in response to an exam type selection made during performance of the ultrasound exam but after receipt of at least some of the exam findings; and wherein the user interface allows a user to readily expand beyond a protocol defined for a currently selected exam type.

12. The ultrasound imaging system of claim 11, wherein the prior exam findings comprise information retrieved from a data repository regarding a prior, non-ultrasound exam.

13. The ultrasound imaging system of claim 11, wherein the program instructions generate the electronic report further including the prior exam findings in response to an indication of clinical relevance of the prior exam findings to the ultrasound exam.

14. A machine-implemented method comprising:

presenting a user interface of a program that supports reporting of a plurality of medical exams available during a diagnostic medical imaging procedure;

receiving information that specifies findings of the diagnostic medical imaging procedure via the user interface;

receiving an exam type selection after receiving the findings information, the exam type selection corresponding to the diagnostic medical imaging procedure conducted and indicating a selected exam type from a plurality of predefined exam types; and loading a set of predetermined findings corresponding to the selected exam type for the diagnostic medical imaging procedure, wherein any of the predetermined findings in the set that conflict with the received findings information are disregarded.

15. The method of claim 14, further comprising receiving additional information that specifies additional findings of the diagnostic medical imaging procedure via the user interface after loading the set of predetermined findings.

16. The method of claim 14, wherein the user interface comprises a single main window and one or more subsidiary windows accessible via the single main window, wherein the single main window summarizes findings information documented in the user interface, including both received specified findings and loaded predetermined findings that correspond to the one or more subsidiary windows.

17. The method of claim 14, further comprising:

identifying a prior exam record for a subject of the diagnostic medical imaging procedure; and tailoring the user interface for presentation based on a time differential between the prior exam and the diagnostic medical imaging procedure being conducted, and based on prior findings of the prior exam.

18. The method of claim 17, wherein the diagnostic medical imaging procedure comprises an obstetrics examination, and tailoring the user interface comprises reconfiguring the user interface for presentation in accordance with a current gestational age computed using a determined gestational age stored in the prior exam record and a difference in time between the prior exam and the obstetrics examination.

19. The method of claim 17, wherein identifying the prior exam record comprises identifying multiple prior examinations of the subject, and tailoring the user interface comprises reconfiguring the user interface for presentation based on a change in associated findings in the multiple prior examinations.

* * * * *